United States Patent [19]

Kit et al.

[11] Patent Number: 4,514,497

[45] Date of Patent: Apr. 30, 1985

[54] MODIFIED LIVE PSEUDORABIES VIRUSES

[75] Inventors: Malon Kit; Saul Kit, both of Houston, Tex.

[73] Assignees: Novagene, Ltd.; Baylor College of Medicine, both of Houston, Tex.

[21] Appl. No.: 567,018

[22] Filed: Dec. 30, 1983

[51] Int. Cl.$^3$ ...................... C12N 7/00; A61K 39/205
[52] U.S. Cl. ...................................... 435/235; 424/89; 435/236
[58] Field of Search ................... 435/235, 236; 424/89

[56] References Cited

U.S. PATENT DOCUMENTS 4,049,794 9/1977 Straub .................................. 424/85

OTHER PUBLICATIONS

Skoda–Acta. Virol., vol. 6, (1962), p. 189.
Skoda et al.–Acta. Virol., vol. 8, (1964), pp. 1–9.
Tenser et al.–J. Gen. Virol., vol. 64, (1983), pp. 1369–1373.
Tenser et al.–J. Clin. Microbiol., vol. 17, No. 1, (1983), pp. 122–127.
Kit et al.–Prog. Med. Virol., vol. 21, (1975), pp. 13–34.
Ben–Porat–Virology, vol. 127, (1983), pp. 194–204.
Feldman et al.–Journal of General Virology, vol. 54, (1981), pp. 333–342.

Primary Examiner—Sam Rosen
Attorney, Agent, or Firm—Gordon Kit

[57] ABSTRACT

Temperature-resistant pseudorabies viruses which fail to produce any functional TK as a result of mutagen-induced mutation and temperature-resistant pseudorabies viruses which fail to produce any functional TK as a result of a deletion in the tk gene, vaccines containing same, methods for production of same and methods for use of same.

39 Claims, 8

PRV(BUK-5) and PRV(BUK-7)

Fig. 5

```
         10        20        30        40        50        60        70        80
GCCCCCGGGGCACGCGCGCGAGGGAGCCGCCGAGTCGCGCAGCTGCACAGCCCCTCGTGCCGCTGCCCGCGCTTGCTGGG 90       100       110       120       130       140       150       160
CGTGTTGAGGTGTCCGGGGGAAGCGGCACGTCTTGAGCTCGATGACGAAGCACAGGTGCGGCCCCACCCCCAGCCGCACC 170       180       190       200       210       220       230       240
ACGCACACGCAGTCGGGGCGGCGCACCCCGAGGTTGACTTCAAAGGCCAGGGTCAAGGACGCCTTCTTAAGCGTCTCGCG 250       260       270       280       290       300       310       320
GCGGAAGCCCGAAGAGACTCTCGCCGTACGCGGACGGGCTCGCGGCGCAGGCGTTCGTAGAAGCGGTTGTGGCCAGCGGA 330       340       350       360       370       380       390       400
TCCCCGCCCGGAAGCGCGCCGGGATGCGCATCCTCCGGATCTACCTCGACGGCGCCTACGGCACCGGCAAGAGCACCACG 410       420       430       440       450       460       470       480
GCCCGGGTGATGGCGCTCGGCGGGGCGCTGTACGTGCCCGAGCCGATGGCGTACTGGCGCACTCTGTTCGACACGGACAC 490       500       510       520       530       540       550       560
GGTGGCCGGTATTTACGATGCGCAGACCCGGAAGCAGAACGGCAGCCTGAGCGAGGAGGACGCGGCCCTCGTCACGGCGC 570       580       590       600       610       620       630       640
AGACCAGGCCGCCTTCGCGACGCCGTACCTGCTGCGTGCACACGCGCCTGGTCCCGCTCTTCGGGCCCGCGGTCGAGGGC 650       660       670       680       690       700       710       720
CCGCCCGAGATGACGGTCGTCTTTGACCGCCACCCGGTGGCCGCGACGGTGTGCTTCGCCGTGGCGCGCTTCATCGTCGG 730       740       750       760       770       780       790       800
GGACATCAGCGCGGCGGCCTTCGTGCCGTGGCGGCCACGCTGCCCGGGGAGCCCCCCGCGGCAACCTGGTGGTGGCCTCG 810       820       830       840       850       860       870       880
CTGGACCCGGACGAGCACCTGCGGCGCCTGCGGCCCGCGCGCGCGCCGGGGAGCACGTGGACGCGCGCCTGCTCACGGCC 890       900       910       920       930       940       950       960
CTGCGCAACGTCTACGCCATGCTGGTCAACACGTCGCGCTACCTGAGCTCGGGGCGCCGCTGGCGCGACGACTGGGGGCG 970       980       990      1000      1010      1020      1030      1040
CGCGCCGCGCTTCGACCAGACCACGCGCGACTGCCTCGCGCTCAACGAGCTCTGCCGCCCGCGCGACGACCCCGAGCTCC 1050      1060      1070      1080      1090      1100      1110      1120
AGGACACCCTCTTCGGCGCGTACAAGGCGCCCGAGCTCTGCGACCGGCGCGGGCGCCCGCTCGAGGTGCACGCGTGGGCG 1130      1140      1150      1160      1170      1180      1190      1200
ATGGACGCGCTCGTGGCCAAGCTGCTGCCGCTGCGCGTCTCCACCGTCGACCTGGGGCCCTCGCCGCGCGTCTGCGCGCG 1210      1220      1230      1240      1250      1260      1270      1280
GCCGTGGCGGCGAGGCGCACGTCGGAGGTGACGGAGTCCGCGTCACGGCGACCACATCCGGCAGTGCGTGTGCGCCTTCA 1290      1300      1310      1320      1330      1340      1350      1360
CGTCGGAGATGGGGGTGTGACCCTCGCCCCTCCCACCCGCGCCGCGGCCGGATGGAGACCGCGACGGAGGCAACGACGAC 1370      1380      1390      1400      1410      1420      1430      1440
GGCGTGGGAGGGGGCTCGGGGCGCGTATAAAGCCATGTGTATGTCATCCCAATAAAGTTTGCCGTGCCCGTCACCATGCC 1450      1460      1470      1480      1490      1500      1510      1520
CGCGTCGTCCGTGCGCCTCCCCGCTGCGCCTCCTGACCCTCGCGGGCCTCTGGCCTCGCGGGGCCGCCGCCTCGCCCCG 1530      1540      1550      1560      1570      1580      1590      1600
GCGCGCCAGGGTGGGCCGCCCTCGCCGCAGGGGTCGCGCCCAGCCGCGGCCCGCGCGGGCCCACCCTGTTCGTCCTGGTC 1610      1620      1630      1640      1650      1660      1670      1680
GGCGGACGCTCCGCGCGGTTCGTCTTCCAGCTCGGCGGGCTGGGGGCGCTCAACGACACGCGATCCGCGGGCACCTGCTC 1690      1700      1710      1720      1730      1740      1750      1760
GGCCGG
```

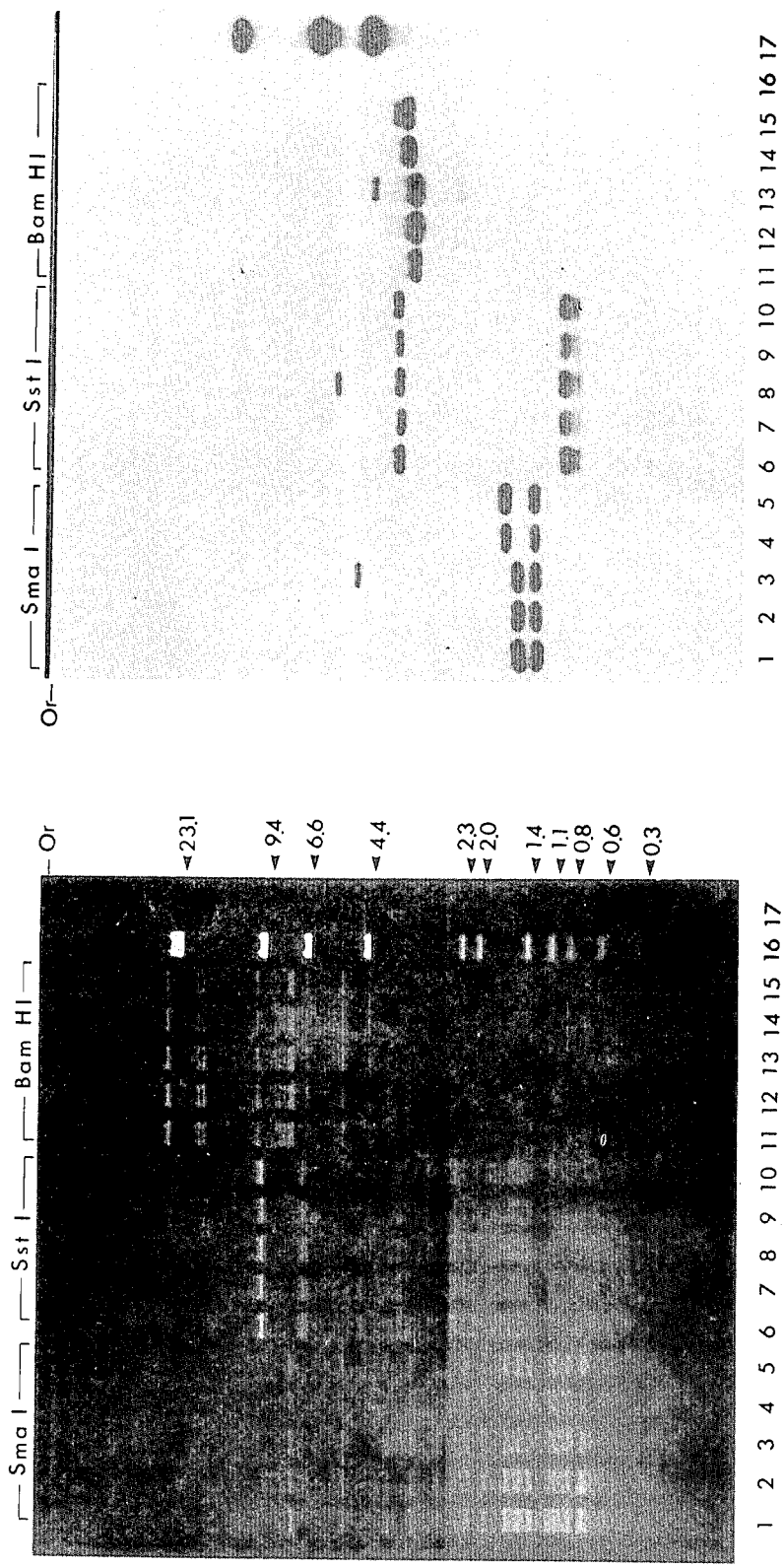

MODIFIED LIVE PSEUDORABIES VIRUSES

FIELD OF INVENTION

The present invention relates to modified live pseudorabies viruses, vaccines for pseudorabies disease containing same, methods for production of same and methods for use of same.

BACKGROUND OF INVENTION

Pseudorabies Disease

Pseudorabies, a highly contagious disease of swine and other livestock, such as cattle, sheep, and goats, is caused by *Herpesvirus suis* (hereinafter "pseudorabies virus" or "PRV"). In swine, the disease causes respiratory illness and encephalitis which may progress to death. Other common consequences of infection in swine are abortions, neonatal demise, reduced litter size, and slower growth rates. In other livestock, most notably cattle, PRV infection almost invariably proceeds to a lethal encephalitis.

Pseudorabies has become a major threat and cause of economic loss to the swine industry throughout the world. There is also considerable alarm over the spread of pseudorabies to cattle and other farm animals. Within the last ten years, economic losses have escalated because of the emergence of more virulent strains of PRV and the widespread dissemination of the disease. Today, it is estimated that 8.0% of the 80 million hogs on farms in the United States are infected, in comparison to less than 0.8% a decade ago.

The clinical symptoms and consequences of PRV infection may be moderated or prevented by the use of vaccines comprising either killed or attenuated strains of PRV. However, existing vaccines have failed to control the spread of pseudorabies disease because of a unique feature of PRV and the other alpha herpesviruses, such as herpes simplex virus types 1 and 2 (hereinafter "HSV-1" and "HSV-2", respectively), varicella-zoster, infectious bovine rhinotracheitis virus (hereinafter "IBRV"), marmoset herpesvirus (hereinafter "MarHV"), and equine herpesvirus type 1.

More specifically, alpha herpesviruses have the special ability to enter into a dormant state, which does not occur with other families of viruses. That is, as an animal recovers from the initial generalized infection, alpha herpesviruses retreat to portions of the nervous system where they become quiescent and impervious to the body's immune defenses. This dormant infection, i.e. latency, may be unexpectedly reactivated, resulting in recrudescence of disease or in a contagious condition known as the carrier state, wherein the infected animal shows no outward symptoms of the disease but can transmit or "shed" infectious alpha herpesviruses intermittently, so as to cause the spread of infection.

Known Modified Live Virus PRV Vaccines

Previous modified live virus PRV vaccines have been produced by multiple passages of the virus in chick and/or monkey tissue culture cells (see: Skoda, R., Brauner, I. Sadecky, E., and Mayer V. *Acta Virol.* 8:1–9 (1964) and Bartha, A. *Magy. Allatorv. Lapja* 16:42–45 (1961)). During tissue culture passages, mutations accumulate as the virus adapts to its new environment. These undefined mutations adversely affect virus reproduction in the natural host, resulting in virus attenuation.

A problem with the currently marketed modified live virus PRV vaccines is that the animal becomes a carrier of the dormant vaccine virus. As a consequence, usage of these vaccines can result in two undesirable situations which impede their safety and effectiveness. First, abortions, stillbirths, and fatal infections in newborns can be caused by some vaccine viruses as they are shed by vaccinated carriers. Second, the repeated circulation of vaccine virus within a herd can result in a reversal of the process of attenuation such that the vaccine virus reverts to the pathogenic parent strain. Under such circumstances, widespread vaccination will undesirably promote the dissemination of the disease.

In addition to the above-described inadequacies, known PRV vaccines, while substantially minimizing symptoms of illness, do not prevent the animal from acquiring a dormant infection with pathogenic field strains. Thus, despite vaccination, an animal may become a carrier of the disease and transmit it to susceptible animals. These carriers of the disease, when moved between farms and market, will shed not only the dormant vaccine virus as discussed above, but also the disease virus. This results in the undesirable transmission of the disease across geographic barriers and state boundaries.

Mode of Action of Alpha Herpesviruses

Upon infection of permissive cells, alpha herpesviruses induce the synthesis of virus-encoded enzymes important to the viral life cycle (see: Kit, S. In: *Pharmacology and Therapeutics.* Ed. A. C. Satorelli; Specialist Subject Ed. D. Shugar (Pergamon Press, Ltd.: Oxford) Vol. 4:501–585 (1979)). Thymidine kinase (hereinafter "TK") is one of the enzymes encoded by the genome of alpha herpesviruses, such as: HSV, IBRV, MarHV, and PRV (see: Dubbs, D. R. and Kit, S. *Virology* 22:493–502 (1964); Kit, S., Leung, W.-C., Jorgensen, G. N., Trkula, D., and Dubbs, D. R. *Progr. Med. Virol.* 21:13–34 (1975); Kit, S. and Qavi, H. *Virology* 130:381A–389 (1983); and Kit, S., Qavi, H., Dubbs, D. R., and Otsuka, H. *J. Med. Virol.* 12:25–36 (1983)). Under normal tissue culture conditions, TK is not essential for virus reproduction. However, TK plays an important role in the pathobiology of infection in animals.

The function of TK is to catalyze the phosphorylation of deoxythymidine to deoxythymidine monophosphate (hereinafter "dTMP") which in turn is further phosphorylated to dTTP, i.e. an essential building block of DNA. TK also indirectly facilitates the synthesis of the other essential building blocks of DNA, i.e. dCTP, dGTP, and dATP. Alpha herpesviruses cannot reproduce themselves without these building blocks (see: Kit, S., Leung, W.-C., Jorgensen, G. N., Trkula, D., and Dubbs, D. R. *Progr. Med. Virol.* 21:13–34 (1975)).

Most tissues of the host produce sufficient amounts of endogenous cell TK, i.e. TK encoded by the genome of the host, to allow for the synthesis of dTMP and dTTP from deoxythymidine and thus allow for viral reproduction. However, non-dividing tissues, such as nerve tissues produce only low levels of endogenous cell TK and thus can only support efficient viral DNA synthesis, and thus viral reproduction, if TK is provided by the infecting virus. The pivotal role of the viral encoded TK in supporting infections of nerve tissues and the establishment of latent infections in ganglia have been demonstrated in studies of HSV, MarHV, and PRV mutants deficient in inducing this enzyme (hereinafer "tk−").

More specifically, HSV tk⁻ mutants have reduced ability to replicate in ganglia or to establish latent infections (see: Field, H. J. and Wildy, P. *J. Hyg., Camb.* 81:267–277 (1978); Field, H. J., Anderson, J. R., and Wildy, P. *J. Gen. Virol.* 59:91–99 (1982); Klein, R. J., DeStefano, E., Brady, E., and Friedman-Kien, A. E. *Arch. Virol.* 65:237–246 (1980); Price, R. W. and Khan, A. *Infect. Immun.* 34:571–580 (1981); and Tenser, R. B., Ressel, S., and Dunstan, M. E. *Virology* 112:328–341 (1981)). In the occasional instance of latent infection, HSV tk⁻ mutants have been difficult to reactivate as detected by the reappearance and shedding of virus. Furthermore, in those instances where the virus has established latency after animals are infected by very large doses of virus, and virus has been reactivated, the shed virus has remained apathogenic, i.e. nonvirulent. Also, the ability of HSV tk⁻ mutants to ascend peripheral nerves into the brain causing encephalitis is drastically curtailed. In addition, intracerebrally injected HSV tk⁻ mutants are comparatively nonvirulent.

Furthermore, mice may be safely inoculated with doses of mutant PRV tk⁻ or mutant MarHV tk⁻ several logs higher than the lethal doses for tk+ viruses (see: Kit, S., Qavi, M. Dubbs, D. R., and Otsuka, H. *J. Med. Virol.* 12:25–36 (1983); and Tenser, R. B., Ressel, S. J., Fralish, F. A., and Jones, J. C. *J. Gen. Virol.* 64:1369–1373 (1983)).

Drug-Induced tk⁻ Viral Mutants

It has been shown that many nucleoside analogs inhibit alpha herpesvirus replication. The antiviral nucleosides include: analogs of thymidine such as 5-bromodeoxyuridine, 5-iododeoxyuridine, 5-fluorodeoxyuridine, trifluorodeoxythymidine, 5-bromovinyldeoxyuridine and 5′-amino-5-iododeoxyuridine (hereinafter "BrdUrd", "IdUrd", "FdUrd", "F$_3$dThd", "BVDU", and "AIdUrd", respectively); analogs of deoxycytidine, such as iododeoxycytidine and briomodeoxycytidine (hereinafter "IdCyd" and "BrdCyd", respectively); arabinosyl analogs of thymidine and deoxycytidine, such as arbinosylthymine, 2′-fluoro-5-iodoarabinosyl cytosine and 2′-fluoro-5-methyl-arbinosyluracil (hereinafter "araT", "FIAC" and "FMAU", respectively); and acyclo derivatives of guanine such as acycloguanosine and 9-1,3-dihydroxy-2-propoxymethyl guanosine (hereinafter "ACG", and "DHPG", respectively) (see: Cheng, Y.-C., Dutschman, G., Fox, J. J., Watanabe, K. A., and Machida, H. *Antimicrob. Agents Chemother.* 20:420–423 (1981); Elion G. B., Furman, P. A., Fyfe, J. A., Demiranda, P., Beauchamp, L., and Schaeffer, H. J. *Proc. Nat. Acad. Sci. USA* 74:5715–5720 (1977); Prusoff, W. E., Chen, M. S., Lin, T.-S., and Fischer, P. H. In: *Antiviral Chemotherapy: Design of Inhibitors of Viral Functions.* Ed. K. K. Gauri. (Academic Press, Inc.: New York), pp. 197–206 (1981); and Veerisetty, V. and Gentry, G. A. *J. Virol.* 46:901–908 (1983)).

The above-described nucleoside analogs differ in their antiviral activities. For example, the concentrations of BVDU and ACG required to inhibit HSV-1 replication are significantly lower than those needed to inhibit HSV-2 replication. Further, FIAC, ACG and DHPG are useful drugs against both HSV-1 and HSV-2, but are ineffective against PRV and IBRV.

The mechanisms by which these drugs inhibit alpha herpesvirus replication vary. However, all of the nucleoside analogs must be activated to nucleoside triphosphates before they can exert their antiviral effects. The first step in this activation requires the catalytic action of the salvage pathway enzyme, TK. In the absence of TK activity, most of these antiviral drugs are not inhibitory.

As stated above, the endogenous cell TK catalyzes the phosphorylation of deoxythymidine to dTMP. The endogenous cell TK also catalyzes the phosphorylation of deoxyuridine to deoxyuridine monophosphate (hereinafter "dUMP"), i.e. a precursor of dTMP. In addition, the endogenous cell TK catalyzes the phosphorylation of several nucleoside analogs, i.e. BrdUrd, IdUrd, FdUrd, F$_3$dThd. Thus, these analogs have cytotoxic as well as antiviral activity. On the other hand, araT, BVDU, FIAC, ACG, and DHPG are poor substrates for the endogenous cell TK. That is, these analogs inhibit viral replication, but not cell replication.

The HSV-encoded TK is remarkable for its broad substrate specificity. That is, the HSV-encoded TK efficiently catalyzes the phosphorylation of deoxythymidine and deoxycytidine and their analogs; arabinosyl derivatives of deoxythymidine and deoxycytidine, such as FMAU and FIAC; ACG and DHPG.

The PRV-encoded TM resembles the HSV-encoded TK in many biochemical properties, but differs from the HSV-encoded TK in antigenic determinants and in substrate specificity (see: Kit, S., Leung, W.-C., Jorgensen, G. N., Trkula, D., and Dubbs, D. R. *Progr. Med. Virol.* 21:13–34 (1975); and Kit, S. In: *Pharmacology and Therapeutics.* Ed. A. C. Sartorelli; Specialist Subject Ed. D. Shugar. (Pergamon Press, Ltd.: Oxford). Vol. 4:501–585 (1979)). That is, the PRV-encoded TK catalyzes the phosphorylation of deoxythymidine analogs, such as BrdUrd, F$_3$dThd; and araT, but does not efficiently phosphorylate deoxycytidine and its analogs; or ACG and DHPG.

After the antiviral drugs are activated to deoxyribonucleoside triphosphates, each is metabolized differently in alpha herpesvirus-infected cells. BrdUrd, IdUrd, and BVdU are extensively incorporated in place of deoxythymidine in viral DNA (see: Allaudeen, H. S., Chen, M. S., Lee, J. J., De Clercq, E., and Prusoff, W. H. *J. Biol. Chem.* 257:603–606 (1982); De Clercq, E. *Arch. Int. Physiol. Biochim.* 87:353–395 (1979); Larsson, A. and Oberg, B. *Antimicrob. Agents Chemother.* 19:927–929 (1981); Prusoff, W. E., Chen, M. S., Lin, T.-S., and Fischer, P. H. In: *Antiviral Chemotherapy: Design of Inhibitors of Viral Functions.* Ed. K. K. Gauri. (Academic Press, Inc.: New York). pp. 197–206 (1981); and Sim, I. S., Goodchild, J., Merdith, D. M. Porter, R. A., Ruper, R. H., Viney, J., and Wadsworth, H. J. *Antimicrob. Agents Chemother.* 23:416–421 (1983)). This incorporation can destabilize the viral genome and later its transcription and translation. The triphosphates of BrdUrd, IdUrd, and BVDU also drastically alter deoxyribonucleoside triphosphate pools. The resulting imbalances in the triphosphate pools can enhance the mutation frequency and/or inhibit another key enzyme of DNA biosynthesis, i.e., ribonucleoside diphosphate reductase (see: Nakayama, K., Ruth, J. L., and Cheng, Y.-C. *J. Virol.* 43:325–327 (1982)).

Triphosphates of many of the analogs, for example, araT, FMAU and FIAC are preferentially bound by alpha herpesvirus DNA polymerases and competitively inhibit the utilization of the natural triphosphates in DNA synthesis (see: Ruth, J. L. and Cheng, Y.-C. *Mol. Pharmacol.* 20:415–522 (1981)). They may also bind to the alpha herpesvirus DNA polymerases forming nondissociable complexes.

The triphosphate of ACG is selectively utilized for DNA synthesis in HSV-infected cells, but terminates DNA chains because the drug lacks a 3'-hydroxy group. AraT, FMAU, and FIAC selectively inhibit HSV DNA synthesis, but are not incorporated significantly into replicating DNA chains.

To avoid the antiviral effects of nucleoside analogs, alpha herpesviruses mutate to drug resistance. Drug-resistant mutants arise spontaneously due to imperfections in the DNA replication mechanisms in all replicating alpha herpesvirus populations with an incidence of about $10^{-3}$ to $10^{-5}$.

Three types of drug-resistant alpha herpesvirus mutants have been detected, i.e. alpha herpesviruses having: (1) a mutation in the viral tk gene; (2) a mutation in the viral DNA polymerase gene; and (3) mutations in both genes.

The mutations in the viral TK and viral DNA polymerase genes can be subdivided into additional classes. That is, some of the viral TK and viral DNA polymerase mutations cause a complete loss of activity, while others only cause a partial loss of activity or selectively diminish the ability of the mutant enzymes to recognize their substrates (see: Veerisetty, V. and Gentry, G. A. *J. Virol.* 46:901–908 (1983); Larder, B. A., Derse, D., Cheng, Y.-C., and Darby, G. *J. Biol. Chem.* 259:2027–2033 (1983); Ruth, J. L. and Cheng, Y.-C. *Mol. Pharmacol.* 20:415–522 (1981); and Sim, I. S., Goodchild, J., Meredith, D. M., Porter, R. A., Ruper, R. H., Viney, J., and Wadsworth, H. J. *Antimicrob. Agents Chemother.* 23:416–421 (1983)).

The most effective mechanism for developing drug resistance is by eliminating any expression of viral TK activity (see: Dubbs, D. R. and Kit, S. *Virology* 22:214–225 (1964); and Dubbs, D. R. and Kit, S. *Virology* 22:493–502 (1964)). That is, alpha herpesvirus mutants, incapable of synthesizing a functional TK polypeptide cannot phosphorylate nucleoside analogs to toxic metabolites regardless of whether or not the viral DNA polymerase is altered. Nevertheless, these mutants can be propagated under normal tissue culture conditions. Thus, cultivation of alpha herpesviruses in the presence of nucleoside analogs permits the selection and enrichment of spontaneous and induced mutants deficient in TK activity.

Several different types of viral TK mutants lacking any TK activity are known. Some of these mutants induce the synthesis of intact, but nonfunctional, TK. These mutants either have changed amino acids at the active centers of the enzyme or mutations that alter polypeptide folding, i.e. a temperature-sensitive TK. Other mutants, e.g. HSV-1 (B2006), fail to induce production of any TK, possibly as a result of nonsense mutations at codons near the amino terminus of the polypeptide. Still other mutants induce inactive, short polypeptides as a result of nonsense mutations in the middle of the tk gene. This type of mutation can be "suppressed" with A"suppressor tRNAs" so that partial TK activity can be restored. Finally, mutants without any TK activity result from the deletion of nucleotides within the coding region of the tk gene.

The first procedure ever used to obtain HSV tk⁻ or vaccinia tk⁻ mutant viruses entailed the propagation of HSV-1 or vaccinia virus in tk⁻ mouse fibroblast cells, i.e., LM(TK⁻) cells, for several passages in growth media containing BrdUrd, and then plaque-purifying the progeny viruses in media containing BrdUrd (see Dubbs, D. R. and Kit, S. *Virology* 22:214–225 (1964); Dubbs, D. R. and Kit, S. *Virology* 22:493–502 (1964); and Kit, S. and Dubbs, D. R. *Biochem. Biophys. Res. Commun.* 13:500–504 (1963)). tk⁻ mutants of HSV-2 (strain 333), PRV (strain Aujeszky), and MarHV (strain Falk) were also later isolated by similar procedures (see: Kit, S., Leung, W.-C., Jorgensen, G. N., Trkula, D., and Dubbs, D. R. *Progr. Med. Virol.* 21:13–34 (1975)).

tk⁻ mutants of HSV-1, HSV-2, PRV, and IIBRV have also been obtained by using tk⁺ tissue culture cells as hosts and noncytotoxic drugs, such as araT, BVDU, and ACG, for selection (see: BenPorat, T., Veach, R. A., and Ihara, S. *Virology* 127:194–204 (1983); Field, H. J., Anderson, J. R., and Wildy, P. *J. Gen. Virol.* 49:91–99 (1982); Field, H. J. and Neden, J. *Antiviral Res.* 2:243–254 (1982); Gordon, Y., Gilden, D. H., Shtram, Y. Asher, T., Tabor, E., Wellish, M., Devlin, M., Snipper, D., Hadar, J., and Becker, Y. *Arch. Virol.* 76:39–49 (1983); Klein, R. J. *Arch. Virol.* 72:143–168 (1982); Larder, B. A., Derse, D., Cheng, Y.-C., and Darby, G. J. *Biol. Chem.* 258:2027–2033 (1983); Tenser, R. B., Ressel, S., and Dunstan, M. E. *Virology* 112:328–341 (1981); and Weinmaster, G. A., Misra, V., McGuire, R., Babiuk, L. A., and De Clercg, E. *Virology* 118:191–201 (1982)).

Besides being highly attenuated, tk⁻ mutants of HSV-1, HSV-2 and MarHV function as effective vaccines. Animals inoculated with these tk⁻ virus mutants resist challenge with lethal doses of tk⁺ viruses (see: Field, H. J. and Wildy, P. *J. Hyg., Camb.* 81:267–277 (1978); Klein, R. J. *Arch. Virol.* 72:143–168 (1982); and Kit, S., Qavi, H., Dubbs, D. R. and Otsuka, H. *J. Med. Virol.* 12:25–36 (1983)). Furthermore, it has been demonstrated for HSV that tk⁻ virus-vaccinated animals are less likely to develop latent infections when challenged with tk⁺ virus.

Many of the alpha herpesvirus tk⁻ drug-induced mutants that have so far been isolated have two shortcomings which make them inappropriate for vaccines. First, the mutants with partial TK activity are virulent (see: Gordon, Y., Gilden, D. H., Shtram, Y., Asher, Y., Tabor, E., Wellish, M., Devlin, M., Snipper, D., Hadar, J., and Becker, Y. *Arch. Virol.* 76:39–49 (1983); Klein R. J. *Arch. Virol.* 72:143–168 (1982); and Tenser, R. B., Ressel, S., and Dunstan, M. E., *Virology* 112:328–341 (1981)). Second, working pools of some of the tk⁻ mutants can contain spontaneous tk⁺ revertants at a frequency of $10^{-3}$ to $10^{-5}$. These tk⁺ revertants can then have a selective advantage for in vivo replication over the tk⁻ mutants. Most drug-induced tk⁻ virus mutants have the potential to revert, even though the reversion frequency may be lower than the spontaneous reversion frequency, i.e. on the order of about $10^{-5}$ to $10^{-7}$ (see: Campione-Piccardo, J., Rawls, W. E., and Bacchetti, S. *J. Virol.* 31:281–287 (1979)).

Deletion-induced tk⁻ Viral Mutants tk⁻ viruses with deletions in the tk gene are superior to tk⁻ mutants containing only nucleotide changes in the tk gene because tk⁻ deletion mutants cannot revert to tk⁺.

Methods for the construction of recombinant HSV-1 tk⁻ or MarHV tk⁻ containing deletions in the coding region of the tk gene are known (see: Smiley, J. R. *Nature* 385:333–335 (1980); Post, L. E., Mackem, S., Roizman, B. *Cell* 24:555–565); and Kit, S., Qavi, H., Dubbs, D. R., and Otsuka, H. *J. Med. Virol.* 12:25–36 (1983)). These deletion mutants are obtained by co-transfecting infectious DNA of HSV-1 tk⁺ or MarHV tk⁺ and hybrid plasmids that contain deleted nucleotide sequences in the corresponding viral tk gene. The resulting recombinant viruses are isolated after plaquing viral harvests in media containing drugs such as araT, BrdUrd and BrdCyd which select for tk⁻ viruses. The tk⁻ deletion viruses are recognized, for example, by analyzing their DNAs with restriction nucleases, by molecular hybridization studies with appropriate probes, and by TK assays on extracts from recombinant virus-infected cells.

In the above-described methods for the construction of alpha herpesvirus tk⁻ deletion mutants, the progeny, which result from the initial co-transfections of cells with tk+ virus DNA and hybrid plasmid DNA, consist of a mixture of viruses. Most of the progeny are parental tk+ viruses and only a very minor portion of the population, i.e. about $10^{-3}$ to $10^{-5}$, consists of recombinant tk⁻ viruses. To isolate the tk⁻ viruses, despite the large excess of tk+ viruses, selection procedures are needed which permit the replication of the tk⁻ viruses while inhibiting the replication of the tk+ viruses. If the selection conditions are extremely effective, that is, there is no associated inhibition of tk⁻ virus replication or breakthrough growth of tk+ virus, then tk⁻ viruses can be selected in a single step. If, however, the selection conditions are only partially effective, then multiple selection steps are needed to enrich for the tk⁻ viruses until they represent a significant fraction of the population.

For HSV-1, efficient selection is possible using BrdUrd, araT, or BrdCyd to prevent plaque formation by HSV-1 tk+. That is, when plaque titrations of mixtures of HSV-1 tk+ and HSV-1 tk⁻ are conducted in media containing these drugs, one HSV-1 tk⁻ out of about $10^3$ to $10^4$ HSV-1 tk+ can be identified and isolated. The resulting HSV-1 tk⁻ plaques are large, well defined, and minimally contaminated with HSV-1 tk+ virus.

However, the above-described procedures are not effective for isolating PRV tk⁻ mutants from a mixture containing a large excess of PRV tk+ because BrdUrd and araT only partially reduce the size and number of PRV tk+ plaques. Further, BrdCyd is ineffective with PRV.

The difference between the response of HSV-1 and that of PRV can be attributed to the dissimilar properties of the PRV and HSV-1 encoded enzymes, i.e. TK, DNA polymerase and ribonucleoside diphosphate reductase; to differences in the composition of the deoxyribonucleoside triphosphate pools of cells infected by the two viruses; and possibly to differences in the ability of PRV and HSV induced nucleases to degrade and utilize cellular DNA for viral synthesis. Thus, in the case of PRV, an enrichment selection step is required to increase the proportion of PRV tk⁻ prior to the isolation of candidate plaques at terminal dilutions in a plaque titration. The need for, use and development of such an enrichment step was not known prior to the present invention.

In summary, while the methods described above are adequate for introducing deletions of foreign DNA sequences into the tk gene of HSV-1 recombinants, they fail to teach or suggest how to introduce deletions into the tk gene of PRV recombinants since: (1) the approximate boundaries of the nucleotide sequences delimiting the coding region of the PRV tk gene have not previously been determined, (2) there is no teaching on the restriction sites within a PRV tk gene to allow appropriate deletions to be made in a cloned PRV tk gene; and (3) as previously discussed, the drugs employed with HSV-1 are inadequate for PRV so that modified enrichment and selection procedures must be developed. Consequently, not only is there insufficient information to use the known procedures for the isolation of deletion mutants in the PRV tk gene, but also the known procedures will not work in the PRV system.

SUMMARY OF THE INVENTION

Accordingly, an object of the present invention is to provide a pseudorabies vaccine effective in controlling the spread of pseudorabies disease.

Another object of the present invention is to provide a pseudorabies vaccine wherein the animal vaccinated with such is less likely to become a carrier of the vaccine virus.

A further object of the present invention is to provide a pseudorabies vaccine wherein the animal vaccinated with such is unlikely to acquire a dormant infection with pathogenic field strains.

A still further object of the present invention is to provide a pseudorabies vaccine wherein the vaccine virus fails to produce any functional TK.

An even further object of the present invention is to provide a pseudorabies vaccine wherein the vaccine virus is a highly attenuated mutagen-induced tk⁻ mutant of pseudorabies virus having a low, i.e. spontaneous, reversion frequency.

An additional object of the present invention is to provide a pseudorabies vaccine wherein the vaccine virus is a tk⁻ deletion mutant of pseudorabies virus which cannot revert to tk+ and is easily isolated from tk+ virus.

Another object of the present invention is to provide a method for the production and use of a highly attenuated mutagen-induced tk⁻ pseudorabies virus having a low, i.e. spontaneous, reversion frequency.

A further object of the present invention is to provide a method for the production and use of a tk⁻ deletion mutant of pseudorabies virus which cannot revert to tk+.

In one embodiment of the present invention, the above-described objects have been met by a temperature-resistant pseudorabies virus which fails to produce any functional TK as a result of mutagen-induced mutation and a modified live virus vaccine for pseudorabies comprising (1) a pharmaceutically effective amount of said virus and (2) a pharmaceutically acceptable carrier or diluent.

In another embodiment of the present invention, the above-described objects have been met by a process for producing a temperature-resistant pseudorabies virus which fails to produce any functional TK as a result of mutagen-induced mutation comprising: (1) plaque-purifying a PRV tk+ strain in tk⁻ host cells at a permissive temperature for a temperature-sensitive virus; (2) propagating the resulting virus of step (1) in tk⁻ host cells 2 to 5 times in the presence of a mutagen at a permissive temperature for a temperature-sensitive virus; (3) propagating the resulting virus of step (2) in tk+ host cells in the presence of a mutagen at a non-permissive temperature for a temperature-sensitive virus; (4) propagating the resulting virus of step (3) in tk+ host cells in the presence of a mutagen at a permissive temperature for a temperature-sensitive virus; (5) propagating the resulting virus of step (4) in tk+ host cells in the presence of a selective agent at a permissive temperature for a temperature-sensitive virus; and (6) propagating the resulting virus of step (5) in tk+ host cells in the presence of a mutagen at a permissive temperature for a temperature-sensitive virus to produce temperature-resistant PRV tk− mutagen-induced mutants.

In a further embodiment of the present invention, the above-described objects have been met by a temperature-resistant pseudorabies virus which fails to produce any functional TK as a result of a deletion in the tk gene and a modified live virus vaccine for pseudorabies comprising (1) a pharmaceutically effective amount of said virus and (2) a pharmaceutically acceptable carrier or diluent.

In still a further embodiment of the present invention, the above-described objects have been met by a process for producing a temperature-resistant pseudorabies virus which fails to produce any functional TK as a result of a deletion in the tk gene comprising: (1) constructing a hybrid plasmid comprising a cloning vector and a DNA fragment of PRV containing substantially all of the PRV tk gene; (2) co-transfecting, in tk+ host cells, the hybrid plasmid of step (1) with DNA from a temperature-resistant PRV tk− mutagen-induced mutant; (3) selecting, in tk− host cells, for PRV tk+ from the virus produced in step (2); (4) deleting DNA sequences from the hybrid plasmid of step (1) such that less than substantially all of the PRV tk gene is present, while retaining PRV DNA sequences adjacent to each side of the deletion; (5) co-transfecting, in tk+ host cells, PRV tk+ DNA derived from the PRV tk+ obtained in step (3) with the resulting hybrid plasmid of step (4); and (6) selecting, in tk− host cells, for PRV tk− from the virus produced in step (5) to produce temperature-resistant PRV tk− deletion mutants.

BRIEF DESCRIPTION OF THE DRAWINGS

FIG. 5 illustrates the nucleotide sequence of a PRV(BUK-7) fragment which contains the coding region of the PRV tk gene and flanking sequences thereof. This sequence is the complement of the DNA strand transcribed to produce PRV TK mRNA.

FIGS. 6A and 6B shows agarose gels of SmaI, SstI, and BamHI fragments of PRV DNA. FIGS. 6A is ethidium bromide-stained. 6B is an autoradiogram showing hybridization of [$^{32}$P]-labeled pBB-11 probe to specific DNA fragments.

DETAILED DESCRIPTION OF THE INVENTION

Figure 1:
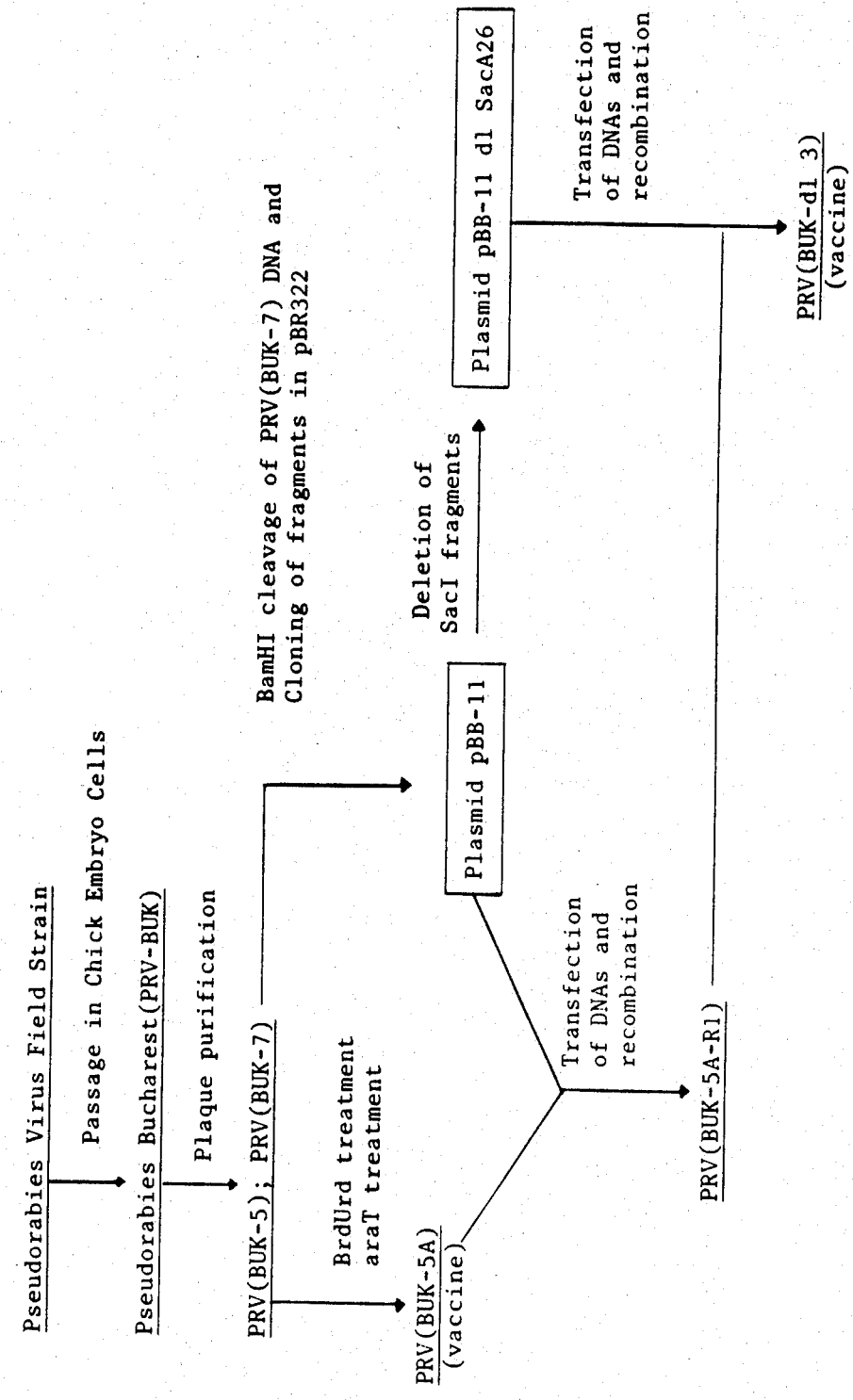
FIG. 1 schematically illustrates, by example, the derivation of pseudorabies virus strains of the present invention.

In one embodiment, the present invention relates to highly attenuated, temperature-resistant PRV tk− mutagen-induced mutants which contain one or more mutations in the tk gene so that the spontaneous reversion rates are less than $10^{-5}$ and the mutant virus does not produce any functional TK, and a process for the production thereof.

This embodiment of the present invention goes beyond a method of merely isolating tk− mutants, but relates to a method for accumulating multiple genetic alterations, such that a reduction in the ability of the virus to cause disease is achieved.

The process of this embodiment of the present invention comprises the following steps: (1) plaque-purifying a PRV tk+ strain in tk− host cells at a permissive temperature for a temperature-sensitive virus; (2) propagating the resulting virus of step (1) in tk− host cells 2 to 5 times in the presence of a mutagen at a permissive temperature for a temperature-sensitive virus; (3) propagating the resulting virus of step (2) in tk+ host cells in the presence of a mutagen at a non-permissive temperature for a temperature-sensitive virus; (4) propagating the resulting virus of step (3) in tk+ host cells in the presence of a mutagen at a permissive temperature for a temperature-sensitive virus; (5) propagating the resulting virus of step (4) in tk+ host cells in the presence of a selective agent at a permissive temperature for a temperature-sensitive virus; and (6) propagating the resulting virus of step (5) in tk+ host cells in the presence of a mutagen at a permissive temperature for a temperature-sensitive virus to produce temperature-resistant PRV tk− mutagen-induced mutants.

Plaque-purification provides a means of purifying the starting materials to be used for vaccine virus formation since field isolates and known attenuated strains often comprise a mixture of different viruses.

The specific PRV tk+ strain employed as a starting material in the present invention is not critical. Examples of such PRV tk+ strains include well-known attenuated strains such as the Bucharest strain (hereinafter "PRV(BUK)"), the SUCH-1 strain (see: Skoda, R., Brauner, I., Sadecky, E., and Mayer, V. *Acta Virol.* 8:1–9 (1964)), the K strain also known as Bartha (see: Bartha, A., *Magy. Allatorv.* Lapja 16:42–45 (1961)), and the Norden strain (see: Paul, P.S., Mengeling, W. L. and Pirtle, E. C. *Arch. Virol.* 73:193–198 (1982)); and virulent strains isolated directly from diseased animals or passaged frequently in the laboratory such as the Aujeszky strain having ATCC No. VR-135 (hereinafter "PRV(Auj)"), the P-2208 strain, the KC-152D strain (see: Maes, R. K., Kanitz, C. L. and Gustafson, D. P. *Am. J. Vet. Res.* 44:2083–2086 (1983)), the S62/26 Iowa strain, the Ind-FH strain, the Ind-S strain, the Ind-R strain and the Shope strain (see: Paul, P. S., Mengeling, W. L., and Pirtle, E. C. *Arch. Virol.* 73:193–198 (1982)). PRV(BUK) is the preferred strain employed in the present invention.

In the context of this invention, a temperature-resistant virus is a virus which is non-temperature sensitive. Thus, a temperature-resistant virus is capable of replicating, at a non-permissive temperature, i.e. about 38.5° C. to 40° C., preferably 39.1° C., about as well as the parental virus or field isolates of PRV replicate at a permissive temperature. By contrast, temperature-sensitive PRV strains contain mutations in viral genes essential for replication, whereby funvctional gene products are produced at permissive temperatures, i.e. about 33° C. to 37.5° C., preferably 34.5° C., but not at non-permissive temperatures. Therefore, in temperature-sensitive viruses, production of infectious virus particles is 4 to 7 logs lower at the non-permissive temperatures compared to production at permissive temperatures. With temperature-resistant virus strains, production of infectious virus particles is about the same at non-permissive temperatures as at permissive temperatures.

Some temperature-sensitive respiratory virus strains, for example, a temperature-sensitive mutant of IBRV, have previously been used as modified live-virus vaccines (see: Pastoret, P. P., Thiry, E., Brocphier, B., and Derboven, G., Ann. Rech. Vet. 13:221-235 (1982) and Chanock, R. M., J. Infect. Dis. 143:364-374 (1981)). The rationale for such use is that the temperature-sensitive virus can undergo limited replication at privileged sites, such as the upper respiratory tract, and elicit local host immunological responses. However, the temperature-sensitive viruses are impaired in replication in the deeper tissues of the host animal, where the temperature is non-permissive for virus replication.

Temperature-resistant viruses are superior to temperature-sensitive viruses as modified live virus vaccines because: (1) attenuation results from alterations in specific pathogenic virus genes rather than from crippling viral genes required for replication; and (2) the temperature-resistant virus strains can replicate more extensively at the site of inoculation and elicit a more complete and prolonged immunological response.

The specific tk$^-$ host cells employed in the present invention are not critical as long as they allow for permissive growth of PRV. Examples of such tk$^-$ host cells include rabbit Rab(BU), mouse LM(TK$^-$), human HeLa(BU25) (see: Kit, S., Qavi, H., Dubbs, D. R. and Otsuka, H. J. Med. Virol. 12:25-36 (1983)), syrian hamster BHK 21 (TK$^-$) (see: Sandus, P. G., Wilkie, N. M. and Davidson, A. J. J. Gen. Virol. 63:277-295 (1982)), and human line 143 (see: Campione-Picardo, Rawls, W. E. and Bacchetti, S. J. Virol. 31:281-287 (1979)). Rab(BU) are the preferred tk$^-$ host cells employed in the present invention.

The specific tk$^+$ host cells employed in the present invention are not critical as long as they allow for permissive growth of PRV. Examples of such tk$^+$ host cells include Rab-9 having ATCC No. 1414; primary rabbit kidney cells; secondary rabbit kidney cells; monkey cells, e.g. CV-1 and OMK; human cells, e.g. HeLa(S3) and human embryonic kidney cells; and chick embryo fibroblast cells. Rab-9 are the preferred tk$^+$ host cells employed in the present invention. However, it should be noted that for the production of virus to be used for vaccination of animals in the field, a United States Department of Agriculture certified cell line permissive for PRV, preferably of the same species as the animal to be vaccinated, and free of other infectious agents, should be used. For example, a suitable porcine cell line would be a certified diploid non-tumorgenic pig kidney cell line free of mycoplasma and other viruses.

The specific mutagen employed in the present invention is not critical. Examples of such mutagens include: BrdUrd, NH$_2$OH, HONO, nitrosoguanidine and UV light (see: Schaffer, P. A., Aron, G. M., Biswal, N. and Benyesh-Melnick, Virology 52:57-71 (1973) and Sandri-Goldin, R. M., Levine, M. and Glorioso, J. C. J. Virol. 38:41-49 (1981)). BrdUrd is the preferred mutagen because of its combined mutagenic and selection activity. That is, BrdUrd is not only a well-known potent mutagen, but it is also useful for selecting tk$^-$ viruses. Serial passages of PRV in low concentrations of BrdUrd allow the virus to grow while mutations therein accumulate. These mutations diminish virulence and thus enhance the safety of the vaccine. Subsequent passages at higher BrdUrd concentrations and in the presence of araT allows for the selection of the tk$^-$ phenotype. The present invention differs from a method recently employed to obtain PRV tk$^-$ mutants since araT was only used therein to obtain drug-resistant PRV (see: Ben-Porat, T., Veach, R. A., and Ihara, S. Virology 127:194-204 (1983)). That is, araT is not a mutagen and thus only selection of spontaneous PRV tk$^-$ mutants occurs by this method. Further, many alpha herpesvirus mutants isolated by araT selection are only partially defective in production of TK and hence are virulent.

By utilizing BrdUrd both as a mutagen and as a selective agent, it is possible to introduce multiple mutations not only in the viral tk gene but throughout the viral genome, and thus to obtain an attenuated PRV mutant lacking any TK activity and exhibiting a low reversion rate, i.e., a reversion rate of about $10^{-5}$ to $10^{-7}$.

The specific selection agent employed in the present invention is not critical as long as the selection agent is able to select for tk$^-$ from tk$^+$ pseudorabies viruses. Examples of such selection agents include: BrdUrd, araT, BVDU, FMAU and AIdUrd. AraT is the preferred selection agent for tk$^+$ host cells since it is nontoxic to these cells. BrdUrd is the preferred selective agent for tk$^-$ host cells.

Similar procedures have also been applied to the isolation of a different tk$^-$ alpha herpesvirus, i.e. IBRV (see: Kit, S. and Qavi, H. Virology 130:381-389 (1983) and U.S. patent application Ser. No. 516,179, filed July 21, 1983). However, in these procedures tk$^-$ host cells were not employed and the starting material was not PRV.

In another embodiment, the present invention relates to temperature-resistant tk$^-$ deletion mutants of PRV which fail to produce any functional TK as a result of a deletion in the tk gene and a process for the production thereof. Since the mutants lack part of the DNA sequence coding for TK, reversion to tk$^+$ does not occur.

The process of this embodiment of the present invention comprises: (1) constructing a hybrid plasmid comprising a cloning vector and a DNA fragment of PRV containing substantially all of the PRV tk gene; (2) co-transfecting, in tk$^+$ host cells, the hybrid plasmid of step (1) with DNA from a temperature-resistant PRV tk$^-$ mutagen-induced mutant; (3) selecting, in tk$^-$ host cells, for PRV tk$^+$ from the virus produced in step (2); (4) deleting DNA sequences from the hybrid plasmid of step (1) such that less than substantially all of the PRV tk gene is present, while retaining PRV DNA sequences adjacent to each side of the deletion; (5) co-transfecting, in tk$^+$ host cells, PRV tk$^+$ DNA derived from the PRV tk$^+$ obtained in step (3) with the resulting hybrid plasmid of step (4); and (6) selecting, in tk$^-$ host cells, for PRV tk$^-$ from the virus produced in step (5) to produce temperature-resistant PRV tk$^-$ deletion mutants.

The tk gene is approximately 1500 bp in size. The deletion mutants can be produced by eliminating a 75 to 1500 bp DNA fragment from an appropriate coding region of the tk gene so that proper folding or substrate binding of the TK is prevented. Alternatively, the deletion mutants can be produced by eliminating a 10 to 100 bp DNA fragment so that the proper reading frame of the gene is shifted. In the latter instance, a nonsense polypeptide may be produced or polypeptide synthesis may be aborted due to a frame-shift-induced stop codon. The preferred size of the deletion is about 75 to 750 bp.

As used herein, "flanking sequences" means the sequences upstream, downstream, or both upstream and downstream, from the tk gene coding sequences. The upstream sequences contain transcriptional control signals, i.e. promoters and enhancers. The downstream sequences contain the polyadenylation signal for transcription of the tk gene.

The precise PRV tk gene sequences which must be present in the hybrid plasmid of step (1) will depend on the sequences chosen for the deletion and the restriction nucleases to be employed in the engineering of the deletion mutant.

The PRV tk$^-$ mutant employed in this embodiment contains one or more point mutations in the coding region of the tk gene. Therefore, the hybrid plasmid to be employed in step (1) must contain PRV tk$^+$ gene sequences to replace the specific sequences mutated in the PRV tk$^-$ mutant. Recombination events between the PRV tk$^-$ DNA and the hybrid plasmid of step (1) have to occur both upstream and downstream from the mutagen-induced mutation(s) in the PRV tk$^-$ gene. Although the crossover events, i.e. marker rescue, by which the hybrid plasmid of step (1) replaces the mutated PRV tk$^-$ DNA might theoretically occur even when the rescuing plasmid PRV DNA fragment is small, e.g. 50 to 100 bp, in practice, marker rescue by such a small DNA fragment is unlikely. By contrast, the probability of marker rescue is greatly increased when the rescuing DNA fragment is about 1 to 4 kb. Note, the PRV DNA insert in pBB-11, described below, is 3.5 kb.

The specific PRV DNA sequences adjacent to the deletion in the plasmid required in step (4) depend on the specifics of the deletion in the hybrid plasmid. In general, the size of the PRV DNA sequences adjacent to both the 3' and 5' sides of the deletion will be at least about 400 bp. For example, in the instance where plasmid pBB-11 dl SacA26, described below, is used for transfection in step (5) with PRV tk$^+$ DNA, the deleted 0.1 kb nucleotide sequence of the PRV tk gene is about 800 bp from the BamHI cleavage site at map unit 2.8 (see FIG. 4). This is sufficient to permit a crossover event on the 5' upstream side of the SacI-C deletion. Likewise, there are 1100 bp in the nucleotide fragment extending from the SacI cleavage site (0.9 map units) to the SacI site (2.0 map units) of pBB-11 dl SacA26 (see FIG. 4). This is more than adequate for the crossover on the 3' downstream side of the SacI-C deletion.

The particular cloning vector employed in this embodiment of the present invention to construct a hybrid plasmid comprising a DNA fragment of PRV containing the PRV tk gene and flanking sequences thereof is not critical as long as the cloning vector contains a gene coding for a selective trait, e.g. drug resistance. Examples of such cloning vectors include pBR322 and pBR322-based vectors (see: Sekiguchi, T., Nishimoto, T., Kai, R. and Sekiguchi, M. *Gene* 21:267–272 (1983)), pMB9, pBR325, pKH47 (Bethesda Research Laboratories), pBR328, pHC79 (Boehringer Manneheim Biochemicals), phage Charon 28 (Bethesda Research Laboratories), pKB11, pKSV-10 (P-L Biochemicals), pMAR420 (see: Otsuka, H., Hazen, M., Kit, M., Qavi, H. and Kit, S. *Virology* 113:196–213 (1981)) and oligo (dG)-tailed pBR322 (New England Nuclear)).

pBR322 is the preferred cloning vector employed in the present invention since the PRV(BUK) BamHI-11 fragment was found, see below, to contain the PRV tk gene and pBR322 has only one BamHI cloning site. Insertion of a DNA fragment at this site inactivates the cloning vector tetracycline gene, but not the ampicillin gene, so that tetracycline-sensitive, ampicillin-resistant hybrid plasmids that are larger than pBR322 due to the insertion can easily be isolated.

Besides BamHI fragments, BglII, BclI, and MboI fragments of PRV can be cloned at the BamHI site of pBR322 because the BglII, BclI, and MboI fragments have the same cohesive ends as BamHI fragments. pMB9, pBR325, pKH47, pBR328, pHC79 and phage Charon 28 DNA also have a single BamHI cloning site. However, the MboI fragments are small and contain only a part of the tk gene, while the BglII fragments are too large to be conviently cloned in any of the cloning vectors except for phage Charon 28.

It has also been found, see below, that the PRV(BUK) KpnI-J$_L$ fragment contains the PRV tk gene. Thus, pKB11, pKSV-10 and pMAR420 are useful cloning vectors for cloning this fragment since they have only one KpnI cloning site. Similarly, oligo (dG)-tailed pBR322 can be employed as the cloning vector with an oligo (dC)-tailed KpnI-J$_L$ fragment of PRV.

Other cloning vectors containing unique cloning sites which are useful in the present invention can be determined upon evaluation of restriction nucleases other than BamHI and KpnI which produce fragments containing the PRV tk gene. Other restriction nucleases which can be employed to produce fragments containing the PRV tk gene, and thus other cloning vectors which can be useful in the present invention, are readily apparent from the PRV tk gene sequence shown in FIG. 5 discussed more fully below.

The specific host employed for growing the plasmids of the present invention is not essential. Examples of such hosts include *E. coli* K12 RR1 (see: Bolivar, F., Rodriguez, R. L., Greene, P. J., Betlach, M. C. Heyneker, H. L., Boyer, H. W., Crosa, J. H., and Falkow, S. *Gene* 2:95–113 (1977)); *E. coli* K12 HB101 (ATCC No. 33694); *E. coli* MM21 (ATCC No. 336780; and *E. coli* DH1 (ATCC No. 33849). *E. coli* K12 RR1 is the preferred host and has an F$^-$ hsd R hsd M genotype.

Similarly, alternative vector/cloning systems could be employed such as plasmid vectors which grow in *E. coli* or *Saccharomyces cerevisiae*, or both, or plasmid vectors which grow in *B. subtilus*, or even vectors such as bovine papilloma virus (ATCC No. 37112) which grow in animal cells such as mouse (ATCC RL1616) (see: Elder, J. T., Spritz, R. A. and Weissman, S. M. *Ann. Rev. Gen.* 15:295–340 (1981) and Ure, R., Grossman, L. and Moldave, K. *Methods in Enzymology* "Recombinant DNA", vol. 101, Part C, Academic Press, N.Y. (1983)).

A pharmaceutically effective amount of the abovedescribed modified live viruses of the present invention can be employed along with a pharmaceutically acceptable carrier or diluent as a vaccine against pseudorabies disease in animals, such as swine, cattle, sheep and goats.

Examples of pharmaceutically acceptable carriers or diluents useful in the present invention include any physiological buffered medium, i.e. about pH 7.0 to 7.4, containing from about 2.5 to 15% serum which does not contain antibodies to PRV, i.e. is seronegative for PRV. Agammaglobulin serum is preferred to serum which contains gammaglobulin. Examples of serum to be employed in the present invention include: swine serum, calf serum, fetal calf serum, horse serum and lamb serum. Agammaglobulin swine serum from pigs seronegative for PRV would be preferred for vaccination of swine and fetal calf serum or agammaglobulin calf serum would be preferred for vaccination of calves. Serum protein such as porcine albumin or bovine serum albumin in an amount of from about 0.5 to 3.0% can be employed as a substitute for serum. However, it is desirable to avoid the use of foreign proteins in the carrier or diluent which will induce allergic responses in the animal being vaccinated.

It is preferred that the modified live viruses of the present invention be stored at a titer of at least $10^6$ to $10^8$ p.f.u./ml at $-70°$ C. to $-90°$ C. or in a lypholized state at $4°$ C. to $-20°$ C. The lypholized virus may be reconstituted for use with sterile distilled water.

The useful dosage to be administered will vary depending upon the age, weight and species of the animal vaccinated and the mode of administration. A suitable dosage can be, for example, about $10^5$ to $5 \times 10^8$ p.f.u., preferably about $10^6$ to $10^7$ p.f.u.

The vaccines of the present invention can be administered intranasally, intramuscularly and subcutaneously. Intramuscularly is the preferred mode of administration.

The following examples are provided for illustrative purposes and are in no way intended to limit the scope of the present invention. Examples 1 and 2 below are schematically illustrated in FIG. 1.

In the following examples, all media and buffer solutions were made up in glass distilled water unless otherwise indicated.

EXAMPLE 1

Production of Temperature-resistant tk⁻ Mutagen-induced Mutants of PRV

PRV(BUK) is a well-known PRV tk+ strain (see: Skoda, R., Brauner, I., Sadecky, E., and Mayer, V. *Acta Virol.* 8:1–9 (1964)) and was employed as the starting material in this example. PRV(BUK) was provided by Dr. Donald P. Gustafson, Department of Veterinary Medicine, Purdue University, Lafayette, Ind. The virus had originally been attenuated by over 800 passages in chick embryo cell cultures and has been used as a vaccine in Europe. This virus is less virulent for calves and swine than field isolates. At Purdue, the virus had also been passaged several times in porcine kidney (PK-15) cells. After receipt, PRV(BUK) was passaged once in Rab-9 cells and plaque purified as described below to obtain PRV(BUK-5) and PRV(BUK-7).

Plaque purification was conducted in the following manner: Each well of a six well plastic Costar tray, 3.5 mm diameter per well, was seeded with 250,000 Rab(BU) cells in 2.5 ml of Eagle's minimal essential medium (AutoPow, APMEM, Flow Laboratories, Inc.) plus 10% (v/v) fetal calf serum, 50 μg/ml neomycin and 2 mM glutamine and 10 mM Hepes buffer, pH 7.3 (hereinafter "growth medium"). The tray was then incubated at 37° C. for 3 days in a humidified $CO_2$ incubator, at which time the cells formed a confluent monolayer.

Virus that had been stored at $-70°$ C. was then thawed and sonicated for 1 min at 4° C. to release virus aggregates from cell debris. Ten-fold serial dilutions diluted at $10^{-4}$, $10^{-5}$ and $10^{-6}$, using duplicate samples for each virus dilution, were made with growth medium.

Prior to infecting the Rab(BU) cells with the serially diluted PRV(BUK), the growth medium from the Costar wells was aspirated off. Then, a 0.1 ml inoculum of each of the serially diluted virus samples was added to a cell monolayer. After a 1 hr absorption period at 34.5° C., 2.5 ml of an agar overlay solution was added to each well.

The agar overlay solution was prepared as follows: One hundred ml of 2.5% (w/v) BactoAgar (DIFCO) was melted in a boiling water bath. Next, an equal volume (100 ml) of double-strength McCoy's 5A solution (Flow Laboratories, Inc.) was added to the melted agar. Double-strength McCoy's 5A solution contains 2X-Hank's balanced salt solution comprising 280 mM NaCl and 0.67 mM $Na_2HPO_4$, 0.88 mM $KH_2PO_4$, 11 mM KCl, 1.6 mM $MgSO_4(7H_2O)$, 2.5 mM $CaCl_2$, 11 mM glucose, pH 7.12 and phenol Red (4 mg/100 ml) (hereinafter "BSS"), an enriched mixture of amino acids and vitamins, 0.2% (w/v) sodium bicarbonate, and 0.4% (w/v) glucose. Then, the above 200 ml solution was supplemented with 2.0 ml of 200 mM glutamine, 1.0 ml of a solution of 10 mg/ml neomycin, 1.0 ml of mycostatin (10,000 units/ml), 2.4 ml of 1.0M Hepes buffer, pH 7.3, 8.0 ml of a 1.0% (w/v) protamine sulfate solution and 20 ml of fetal calf serum to produce the agar overlay.

After allowing the agar overlay to solidify, the Costar tray was placed in a $CO_2$ incubator at 34.5° C. for 3 days. A second agar overlay was then added.

The second agar overlay had the same composition as the first agar overlay, except that it was supplemented with 10 ml of 0.1% (w/v) neutral red indicator dye. The tray was then returned to the incubator and kept at 34.5° C. for another 12–24 hr.

Virus plaques, i.e., clear white areas against a pink background, were detected. The plaques resulted from successive rounds of replication of a single virus particle with accompanying destruction of a cluster of cells. In contrast, intact non-infected cells stained pink and were clearly visible by microscopy. The plaques were then counted and the virus in a specific plaque was "picked" by inserting a capillary pipette into the agar over the plaque and aspirating and dispensing the material into 0.5 ml of growth medium. The "picked" plaques contained virus in an amount of from about $10^4$ to $10^5$ p.f.u./ml and were stored at $-70°$ C. In this manner, viral clones PRV(BUK-5) and PRV(BUK-7) were obtained.

PRV(BUK-5) and PRV(BUK-7) were found to be genetically identical, having identical restriction nuclease maps. Further, enzyme assays have demonstrated that both PRV(BUK-5) and PRV(BUK-7) induce viral TK activity in cells infected with such at a multiplicity of infection (hereinafter "m.o.i.") of 3 to 5 p.f.u./cell for 6 hr at 37° C. In the procedures described below, PRV(BUK-5) and PRV(BUK-7) could be employed interchangeably.

Working stocks of virus from the "picked" plaques were prepared by infecting monolayer cultures of about $10^7$ Rab-9 cells with 0.5 ml of virus from each plaque picked and incubating at 34.5° C. for 3–5 days until extensive cytopathic effects were observed.

Next, confluent monolayer cultures of Rab(BU) cells (see: Kit, S. and Qavi, H. *Virology* 130:381–389 (1983)) in growth medium were inoculated with PRV(BUK-5) at a m.o.i. of 2.0 p.f.u./cell.

After a 1 hr absorption period at 37° C., the medium was supplemented with 5.0 μg/ml BrdUrd (Calbiochem-Behring Corp.) and the virus was propagated at 34.5° C. for 2 days and harvested by freezing infected cultures at −40° C. in a horizontal position, followed by thawing, shaking to dislodge the infected cells from the glass, mixing the suspension by pipetting up and down and placing aliquots of the growth-medium-containing cell debris in sterile, two-ounce prescription bottles.

Immediately prior to the second passage, described below, one bottle of virus was thawed and sonicated for 1 min at 4° C. using the Sonicator Cell Disrupter Model W220F (Heat Systems Ultrasonics Inc.).

Next, a second passage of a 1:100 dilution of the above harvested virus was conducted in Rab(BU) cells at 34.5° C., except that the growth medium was supplemented with 10 μg/ml BrdUrd.

Then, a third passage of a 1:100 dilution of the virus harvested after the second passage was conducted in Rab(BU) cells at 34.5° C., except that the growth medium was supplemented with 25 μg/ml BrdUrd.

Thereafter, a fourth passage of a 1:500 dilution of the virus harvested after the third passage was conducted in Rab(BU) cells at 34.5° C., except that the growth medium was supplemented with 25 μg/ml BrdUrd. The resulting virus was stored at −70° C. in growth medium and plaque-purified as described above.

The resulting plaque-purified virus was then propagated in growth medium containing 10 μg/ml BrdUrd at both 39.1° C. and 34.5° C. in Rab-9 cells. This step was employed in order to induce additional random mutations in the PRV genome and to select for a virus capable of growth in a tk+ cell at 39.1° C., despite the presence of BrdUrd in the growth medium, i.e., a temperature-resistant BrdUrd-resistant tk− virus.

Rab-9 cells have a TK that phosphorylates BrdUrd. Thus, the virus must not only be tk− since the products of cellular TK activity can also inhibit virus replication, but, also, the virus must be drug-resistant, i.e. BrdUrd-resistant. Only virus which grew equally well at both temperatures, i.e. a nontemperature-sensitive virus or "temperature-resistant" virus, was processed further.

An araT selection step was then employed to ensure that the PRV was cross-resistant to very high concentrations of a nucleoside analog other than BrdUrd. AraT was also used because, unlike BrdUrd, it is phosphorylated selectively by the PRV TK, but not by the Rab-9 TK.

In the araT selection step, 1.0 ml of a 1:200 dilution of the temperature-resistant virus was used to infect confluent monolayer cultures of Rab-9 cells in growth medium using a 1 hr absorption at 37° C. Growth medium containing 100 μg/ml araT (Yamasa Shoyu Co.) was then added and incubation at 34.5° C. was allowed to proceed until extensive cytopathic effects were observed.

Another selection step was conducted as above in Rab-9 cells at 34.5° C. except that the growth medium was supplemented with 200 μg/ml araT.

Next, a selection step was conducted as above in Rab-9 cells at 34.5° C., except that the growth medium was supplemented with 25 μg/ml BrdUrd to ensure that the resulting virus was highly resistant to BrdUrd even in tk+ host cells.

The harvested virus from the last step above was plaque-purified on Rab-9 cells as described above and individual plaques were picked and tested for growth at both 39.1° C. and 34.5° C. in Rab-9 cells so as to select for temperature-resistant and tk− virus clones. One such clone, which has been designated as PRV(BUK-5A), has been deposited at the American Type Culture Collection under ATCC No. VR-2078.

EXAMPLE 2

Production of Temperature-resistant tk− Deletion Mutants of PRV

A. Purification of PRV DNA

PRV DNA was prepared essentially as described by Pignatti et al for the preparation of HSV DNA (see: Pignatti, P. F., Cassai, E., Meneguzzi, G., Chemciner, N. and Milanesi, G. *Virology* 93:260–264 (1979)).

More specifically, 20 8-ounce prescription glass bottle monolayer cultures of Rab-9 cells (about $5 \times 10^6$ cells/culture) containing 20 ml of growth medium were infected at a m.o.i. of 5.0 p.f.u./cell of PRV(BUK-7), produced as in Example 1 above, and incubated for 3 hr at 34.5° C., at which time cellular DNA synthesis had been inhibited by the viral infection. Then 1.0 μCi/ml and 0.25 μg/ml of [$^3$H]thymidine was added to radioactively label the viral DNA and incubation was continued at 34.5° C. for 17 hr more. The cells were dislodged from the glass by scraping into the growth medium with a rubber policeman, centrifuged at $600 \times g$, washed with ice cold phosphate-buffered saline solution comprising 0.14M NaCl, 0.003M KCl, 0.001M $CaCl_2$, 0.0005M $MgCl_2$, and 0.01M phosphate, pH 7.5 (hereinafter "PBS"), containing 10 μg/ml non-radioactive thymidine. Next, the cells were centrifuged at $600 \times g$ and then frozen in an ethanol-dry ice bath.

After thawing, the cell pellet (about 0.7 ml) was resuspended in 9 volumes of lysing solution comprising 0.25% (w/v) Triton X-100, 10 mM EDTA, 10 mM Tris-HCl, pH 7.9. Next, the cell suspension was transferred to a Dounce homogenizer, and incubated at room temperature for 20–30 min with gentle mixing.

Then, the cell suspension was transferred to a glass centrifuge tube and NaCl was added to a final concentration of 0.2M. Next, the tube was inverted several times, and the solution was immediately centrifuged at $1000 \times g$ at 4° C. for 10 min.

The resulting supernatant was decanted into a glass tube and deproteinized by incubating with 100 μg/ml proteinase K (E. M. Science) in buffer solution comprising 10 mM Tris-HCl, pH 7.5, 1.0 mM EDTA (hereinafter "TE buffer") for 1 hr at 37° C. Then, 1 volume of 90% (v/v) redistilled phenol was added, the solution was mixed by inversion, centrifuged at $20,000 \times g$, and the aqueous phase, i.e., top phase, was transferred to a polyallomer centrifuge tube. Solid sodium acetate was then added to a concentration of 4% (w/v), the nucleic acids were precipitated with 2 volumes of ice cold ethanol, and incubated overnight at −20° C. Thereafter, the precipitate was collected by centrifugation at 16,000 rpm at 4° C. in a Spinco SW25 rotor, dissolved in 2.0 ml TE buffer, and dialyzed at 4° C. against TE buffer.

The resulting DNA solution was then transferred to a polyallomer centrifuge tube and CsCl in TE buffer was added to 57% (w/w) ($\rho = 1.715$ g/cm$^2$). Next, the DNA was centrifuged for 46 hr at 22.5° C. at 44,000 rpm in a Spinco No. 50 Ti rotor. Then, 12 drop fractions were collected from the bottom of the polyallomer tube and aliquots of 4.0 μl were counted in a liquid scintillation spectrometer to locate the PRV DNA containing fractions ($\rho$=about 1.727 g/cm$^2$). When a total of 25 fractions were collected, generally fractions 13–15 contained the PRV DNA.

The PRV DNA containing fractions were then pooled and dialyzed against several changes of TE buffer at 4° C. for about 24 hr. The concentration of DNA was determined fluorometrically. The PRV(BUK-7) DNA yield was about 50 μg from 10$^8$ cells.

The identity of the PRV(BUK-7) DNA was verified by the pattern of restriction nuclease-digested PRV(BUK-7) DNA fragments obtained after electrophoresis at 4° C. in a submarine gel apparatus (Bethesda Research Laboratories, Inc.) as described below.

More specifically, DNA was cleaved with BamHI and KpnI restriction nucleases under the reaction conditions recommended by the manufacturer (New England BioLabs, Inc.). Next, 1/10 volume of a solution comprising 0.4% (w/v) bromophenol blue, 125 mM EDTA and 50% (v/v) glycerol was added to terminate the reaction, followed by heating at 65° C. for 10 min. Twenty μl aliquots of each sample was applied into the sample wells of the agarose gel and electrophoresis was carried out as described below.

Figure 2:
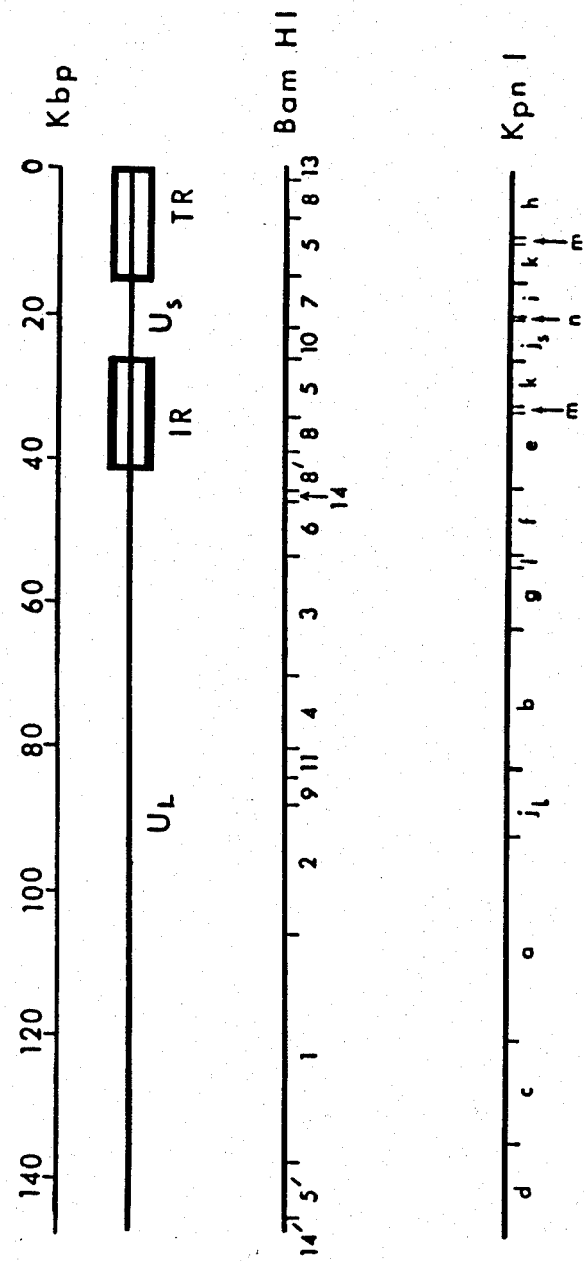
FIG. 2 illustrates PRV(BUK-5) and PRV(BUK-7) DNA restriction nuclease maps for BamHI and KpnI. The inverted repeats (IR) and terminal repeats (TR) which bracket the unique short ($U_S$) region of the genome are shown. $U_L$ signifies the unique long region of the genome.
Figure 3A:
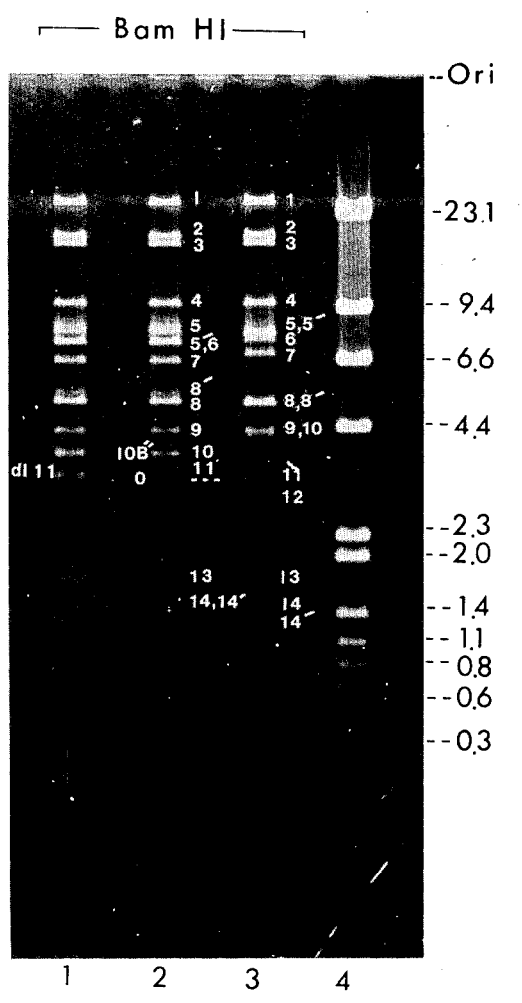
FIGS. 3A and 3B shows ethidium bromide stained agarose gels of BamHI (FIG. 3A) and KpnI (FIG. 3B) digested PRV(Auj), lanes 3 and 8; PRV(BUK-5), lanes 2 and 7; and PRV(BUK-dl 3), lanes 1 and 6. Lanes 4 and 5 contain HindIII λ and HaeIII ΦX174 marker fragments.
Figure 3B:
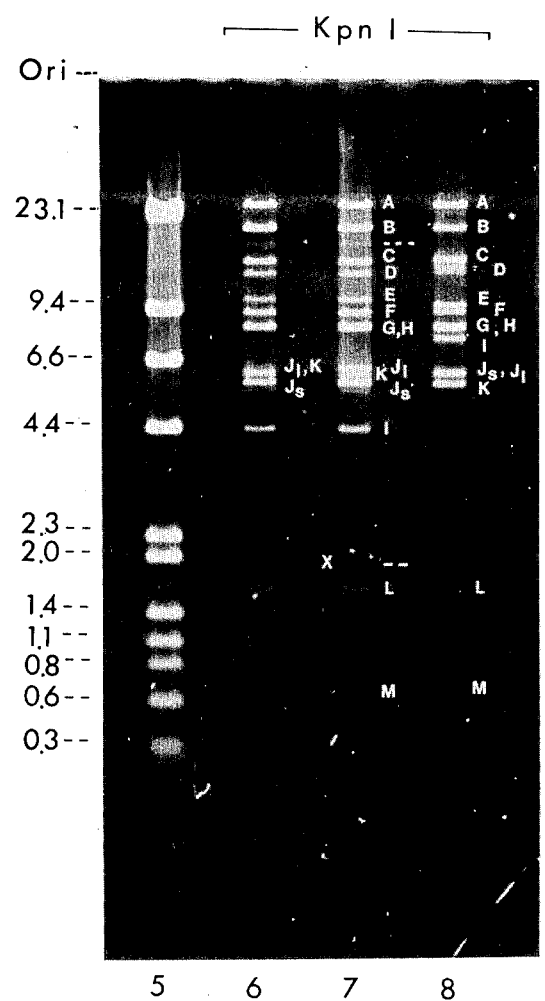

Electrophoresis of restriction nuclease fragments was carried out on 0.6% (w/v) agarose slab gels (see: Kit, S., Qavi, H., Dubbs, D. R. and Otsuka, H. *J. Med. Virol.* 12:25–36 (1983)) in electrophoresis buffer comprising 30 mM NaH$_2$PO$_4$, 1.0 mM EDTA, 40 mM Tris-HCl, pH 8.1 (hereinafter "electrophoresis buffer") at 45 volts, 4° C. for about 16 hr. After electrophoresis, DNA fragments were stained by soaking the gel in electrophoresis buffer containing 0.5 μg/ml ethidium bromide, visualized over a long wave UV illuminator, and photographed. The restriction nuclease pattern and map of PRV(BUK-5) and PRV(BUK-7) are shown in FIGS. 2, 3A and 3B and the sizes of the fragments are shown in Table 1 below.

PRV(BUK-7) DNA prepared in this manner had an infectivity of about 1000 p.f.u. per μg DNA in the standard transfection assay (see: Graham, F. L. and Van der Eb, A. J. *Virology* 52:456–467 (1973)).

TABLE 1

SIZE OF BamHI AND KpnI RESTRICTION FRAGMENTS OF PRV(BUK-5) AND PRV(BUK-7)

| BamHI fragment | kb | KpnI fragment | kb |
|---|---|---|---|
| 1 | 30.3 | A | 29.0 |
| 2 | 17.8 | B | 21.4 |
| 3 | 16.7 | C | 14.5 |
| 4 | 9.8 | D | 13.0 |
| 5 | 8.2 | E | 10.4 |
| 5 | 8.2 | F | 9.4 |
| 5' | 7.5 | G | 8.6 |
| 6 | 7.5 | H | 8.6 |
| 7 | 6.7 | I | 4.4 |
| 8 | 5.1 | J$_L$ | 6.3 |
| 8 | 5.1 | J$_S$ | 5.9 |
| 8' | 5.5 | K | 5.9 |
| 9 | 4.3 | K | 5.9 |
| 10 | 3.8 | L | 1.7 |
| 11 | 3.5 | M | 0.7 |
| 13 | 1.7 | M | 0.7 |
| 14 | 1.4 | N | 0.5 |
| 14' | 1.4 | — | — |
| 15 | 1.0 | — | — |
| 16 | 0.8 | — | — |
| TOTAL: | 146.3 | TOTAL: | 146.9 |

Fragments generated by inversion of L segment:
BamHI Z = 3.2 kb

Fragments generated by inversion of L segment:
KpnI X = 1.9

TABLE 1-continued

SIZE OF BamHI AND KpnI RESTRICTION FRAGMENTS OF PRV(BUK-5) AND PRV(BUK-7)

| BamHI fragment | kb | KpnI fragment | kb |
|---|---|---|---|
| BamHI 10B" = 3.8 kb | | KpnI D + H = 21.6 | |
| BamHI 10B" = BamHI(8'-13) | | | |

B. Cloning of PRV(BUK-7) DNA

BamHI fragments of DNA isolated from PRV(BUK-7) were cloned at the BamHI cleavage site of pBR322 by the following procedure.

4.0 μg DNA from PRV(BUK-7) was dissolved in cutting buffer comprising 150 mM NaCl, 6.0 mM Tris-HCl, pH 7.9, 6.0 mM MgCl$_2$ (hereinafter "cutting buffer"), and 100 μg/ml bovine serum albumin (hereinafter "BSA"). The DNA was then digested at 37° C. for 1 hr with 40 units of BamHI. The reaction was terminated by adding an equal volume of 90% (v/v) redistilled phenol, mixing, and centrifuging for phase separation. After dialysis of the aqueous phase against 0.1×TE buffer, sodium acetate was added to 0.1M followed by the addition of 2 volumes of ethanol, and the DNA precipitate was stored at −20° C. overnight. The DNA precipitate was collected by centrifugation and dissolved in 0.1×TE buffer.

The restriction nuclease fragments were then combined with pBR322 which had been cleaved with BamHI and dephosphorylated in the following manner:

4.0 μg of BamHI-cleaved PRV(BUK-7) DNA was mixed with 0.2 μg of BamHI-digested, dephosphorylated pBR322 DNA (New England BioLabs), in 0.05 ml of ligation buffer solution comprising 50 mM Tris HCl, pH 7.8, 10 mM MgCl$_2$, 20 mM dithiothreitol, 1.0 mM ATP, and 50 μg/ml BSA, and containing 1000 units of phage T4 DNA ligase (New England BioLabs, Inc.), and incubated overnight at 4° C. The reaction was terminated by adding EDTA to 20 mM and heating at 65° C. for 30 min.

The recombinant plasmid DNA was diluted in TE buffer and used to transform *E. coli* K12 RR1 bacteria as described below (see: Bolivar, F., Rodriguez, R. L. Greene, P. J., Betlach, M. C., Heyneker, H. L., Boyer, H. W., Crosa, J. H., and Falkow, S. *Gene* 2:95–113 (1977)).

Bacteria were prepared for transformation using CaCl$_2$ (see: Mandel, M. and Higa, A. *J. Mol. Biol.* 53:159–162 (1970)). Specifically, an overnight culture at a density of 2.0 (A$_{600}$) of *E. coli* K12 RR1 was used to inoculate 200 ml of broth comprising 1.0% (w/v) bactotryptone, 0.5% (w/v) yeast extract, and 0.5% (w/v) NaCl (hereinafter "ML broth"), at a bacterial density of 0.02 (A$_{600}$). The bacteria were incubated for about 2 hr until a density of about 0.5 (A$_{600}$) was achieved. The bacteria were then pelleted by centrifugation and resuspended in ¼ volume of cold 50 mM CaCl$_2$. After a 5 min incubation on ice, the bacteria were again pelleted and resuspended in 1/40 the volume of ice cold 50 mM CaCl$_2$.

Next, 1/10 ml of the recombinant plasmid DNA, about 10–100 ng, in TE buffer was added to 0.2 ml of the CaCl$_2$-treated bacteria. The mixture was kept at 4° C. for 30 min. Then, the temperature was raised to 37° C. for 5 min and 0.3 ml of ML broth was added. Thereafter, incubation was continued for 45 min at 37° C. with gentle shaking. Samples were plated on trypticase soy agar plates (BBL Microbiology Systems) supplemented with 30 μg/ml ampicillin.

Rapid screening of the resulting clones for the desired recombinant plasmid DNA was conducted as follows:

An overnight culture of bacteria containing recombinant plasmid DNA was inoculated into 5.0 ml of ML broth containing 30 μg/ml ampicillin and incubated at 37° C. to a density of about 1.5 ($A_{600}$). One ml of this bacterial culture was then transferred to a 1.5 ml Eppendorf polypropylene tube and centrifuged in an Eppendorf centrifuge for about one minute at room temperature to pellet the bacteria. Next, the bacteria were resuspended in 0.1 ml of lysozyme solution No. 1 comprising 2 mg/ml egg lysozyme; 50 mM glucose; 10 mM cyclohexanediamine tetraacetate; and 25 mM Tris-HCl buffer, pH 8.0 (hereinafter "lysozyme solution No. 1") and then incubated for 30 min at 4° C. Next, 0.2 ml of 0.2N NaOH plus 1.0% (w/v) sodium dodecylsulfate was added to the bacterial suspension and the tube was vortexed and kept at 4° C. for 5 min. Thereafter, 0.15 ml of 3.0M sodium acetate, pH 4.8, was added, and the tube was gently inverted, during which time a "clot" of DNA formed. The DNA was kept at 4° C. for 1 hr to allow chromosomal DNA, protein, and high molecular weight RNA to precipitate. Next, the precipitate was centrifuged in an Eppendorf centrifuge for 5 min at room temperature and the clear supernatant fluid, approximately 0.4 ml, containing recombinant plasmid DNA was transferred to a second Eppendorf centrifuge tube. Then, 2½ volumes of ethanol (approximately 1.0 ml) were added to the second tube which was placed at −20° C. for 30 min. The precipitated recombinant plasmid DNA was collected by centrifugation for 2 min at room temperature in an Eppendorf centrifuge. Then, the recombinant plasmid DNA was dissolved in 0.1 ml of 0.1M sodium acetate, 0.05M Tris-HCl, pH 8.0, reprecipitated with ethanol, collected by again centrifuging, and finally dissolved in 50 μl of water.

Then, a 10 μl aliquot of plasmid DNA was diluted in cutting buffer and 2.0 units of BamHI were added. Following a digestion period of 60 min at 37° C., the sample was mixed with 1/10 volume of a solution comprising 0.4% (w/v) bromophenol blue, 125 mM EDTA and 50% (v/v) glycerol and about 20 μl was applied to a 0.6% (w/v) agarose slab gel for electrophoretic analysis as described above. This analysis revealed whether the recombinant plasmid contained a BamHI insert and, if so, the size, in kb, of the insert (see: Birnboim, H. C. and Doly, J. Nucl. Acids Res. 7:1513–1523 (1973)).

For large-scale preparation of recombinant plasmid DNA, 200 times the amount of plasmid-transformed bacteria were processed as compared with the bacteria used to produce recombinant plasmid DNA for the rapid screening procedure described above, except that after the first ethanol precipitation, the sample was treated, at 37° C. for 30 min, with 0.5 mg of pancreatic RNase A (Worthington Biochemicals) from a stock solution comprising 1.0 mg/ml RNase A in 5.0 mM Tris-HCl pH 8.0 which had been heated at 100° C. for 10 min. The treatment was followed by the addition of 500 μg of proteinase K (E. M. Science) in TE buffer at 37° C. for 30 min. Subsequently, an equal volume of phenol was added, the sample was vortexed and centrifuged as described above to separate the phases. The aqueous phase was then removed, precipitated with ethanol and collected by centrifugation as described above. The precipitate was then dissolved in 0.2 ml of TE buffer and layered on a 10.4 ml linear 10–40% (w/v) sucrose gradient in 50 mM NaCl, 10 mM Tris-HCl, pH 7.5, 1.0 mM EDTA, and was then centrifuged at 4° C. for 20 hr at 24,000 rpm in a Spinco SW41 rotor. Fifteen drop fractions were collected from the bottom of polyallomer centrifuge tubes into wells of plastic trays. A total of 35 fractions was obtained. Five μl aliquots were then screened by employing agarose gel electrophoresis as described above. Fractions containing recombinant plasmid DNA were pooled, dialyzed against 0.1×TE buffer, and stored at 4° C. for further studies.

C. Identification by Marker Transfer of the PRV(BUK-7) DNA Fragment Encoding the tk Gene Homologous recombination in animal cells between purified viral DNA fragments, or by viral DNA fragments amplified by cloning in plasmid vectors, and genomic viral DNA has been used to rescue mutant sequences in either the DNA fragment or the viral genome. The procedure, known as "marker rescue" or "marker transfer", has been employed to map spontaneous mutations and mutations induced by mutagens in the entire viral DNA, as well as to "transfer" mutations from hybrid plasmids into genomic viral DNA (see: Matz, B., Subak-Sharpe, J. H. and Preston, V. G., J. Gen. Virol. 64:2261–2270 (1983)).

Marker transfer procedures were used to identify the PRV(BUK-7) BamHI fragment which encodes the tk gene. That is, a mixture of infectious PRV(BUK-5A) DNA and candidate recombinant plasmids containing different inserts of PRV(BUK-7) BamHI fragments were co-transfected into Rab-9 cells by the calcium phosphate precipitate method (see: Graham, F. L. and Van der Eb, A. J. Virology 52:456–467 (1973)). Specifically, the following sterile solutions were added to a test tube in sequential order:

(1) 0.02 ml of a 100 μg/ml solution of PRV(BUK-5A)DNA in TE buffer;

(2) 0.4 ml of a 10 μg/ml solution of recombinant plasmid containing PRV(BUK-7) BamHI fragments DNA in 0.1×TE buffer;

(3) 0.25 ml of water;

(4) 0.2 ml of a 100 μg/ml solution of carrier mouse fibroblast (LM(TK−)) cell DNA in TE buffer;

(5) 0.125 ml of 2.0M $CaCl_2$; and (6) 1 ml of 2×BSS.

The resulting solution was mixed by inversion and kept at room temperature for 30 min while a DNA-calcium phosphate precipitate formed. Then, 0.5 ml of the suspension containing precipitated DNA-calcium phosphate was added directly to 5.0 ml of growth medium and plated on Rab-9 cells which had been seeded in 60 mm plastic Petri dishes 36 hr earlier. The cells were incubated at 37° C. for 5 hr. Then, fresh growth medium was added and the cultures were further incubated at 34.5° C. for 2–3 days until extensive cytopathic effects occurred. Virus harvests were made as described above.

The resulting virus contained a small number of recombinant PRV tk+. To enrich for recombinant tk+ viruses, the harvests were passaged in Rab(BU) cells, i.e. tk− cells (see: Kit, S. and Qavi, H. Virology 130:381–389 (1983)) in growth medium containing $10^{-4}$ hypoxanthine, $10^{-6}$M aminopterin, $4.0 \times 10^{-5}$M thymidine, and $10^{-5}$M glycine (hereinafter "HATG") (see: Littlefield, J. W. Science 145:709–710 (1964); Littlefield, J. W. Biochim. Biophys. Acta 95:14–22 (1965); and Szybalska, E. H. and Szybalski, W. Proc. Nat. Acad. Sci. USA 48:2026–2034 (1962)) as follows.

The virus harvests of the transfection in Rab-9 cells were sonicated and diluted 1:500 in growth medium containing HATG, and confluent monolayer cultures of Rab(BU) were inoculated with virus at an m.o.i. of about 0.01. After a 1 hr absorption at 37° C., fresh growth medium containing HATG was added and the infection was allowed to progress for 48 hr at 34.5° C., at which time virus harvests were again made. A second selection step was conducted in the same manner, except that the virus was diluted 1:5000. The harvested virus from the second selection passage was plaque-purified in Rab-9 cells as described above (see: Kit, S., Qavi, H. *Virology* 130:381-389 (1983); and Kit, S., Qavi, H., Dubbs, D. R., and Otsuka, H. *J. Med. Virol.* 12:25-36 (1983)). As shown in Table 2 below, a recombinant plasmid that was tested by the marker transfer method, i.e. plasmid pBB-11, rescued the tk$^-$ mutation of PRV(BUK-5A), i.e. recombined with PRV(BUK-5A) to produce a tk$^+$ virus designated PRV(BUK-5A R1). In contrast, as shown in Table 2 below, plasmids containing PRV DNA fragments BamHI-4 and BamHI-9, which map on either side of the BamHI-11 fragment (see FIG. 2), i.e. plasmids pBB-4 and pBB-9, respectively, did not rescue the tk$^-$ mutation of PRV(BUK-5A). These results demonstrate that the BamHI-4 and BamHI-9 fragments do not contain sequences covering the mutation sites in the PRV(BUK-5A) tk gene.

TABLE 2

Marker Transfer of PRV tk$^+$ Gene From Hybrid Plasmid pBB-11 to PRV(BUK-5A)

| Group | DNA used for transfection | PRV titer after two selective passages in HATG (p.f.u./ml) |
|---|---|---|
| I | PRV(BUK-5A) DNA only (control) | $1.0 \times 10^3$ |
| II | PRV(BUK-5A) DNA plus plasmid pBB-11 DNA | $3.2 \times 10^7$ |
| III | PRV(BUK-5A) DNA plus plasmid pBB-4 DNA | $7.0 \times 10^2$ |
| IV | PRV(BUK-5A) DNA plus plasmid pBB-9 DNA | $2.0 \times 10^3$ |

Figure 4:
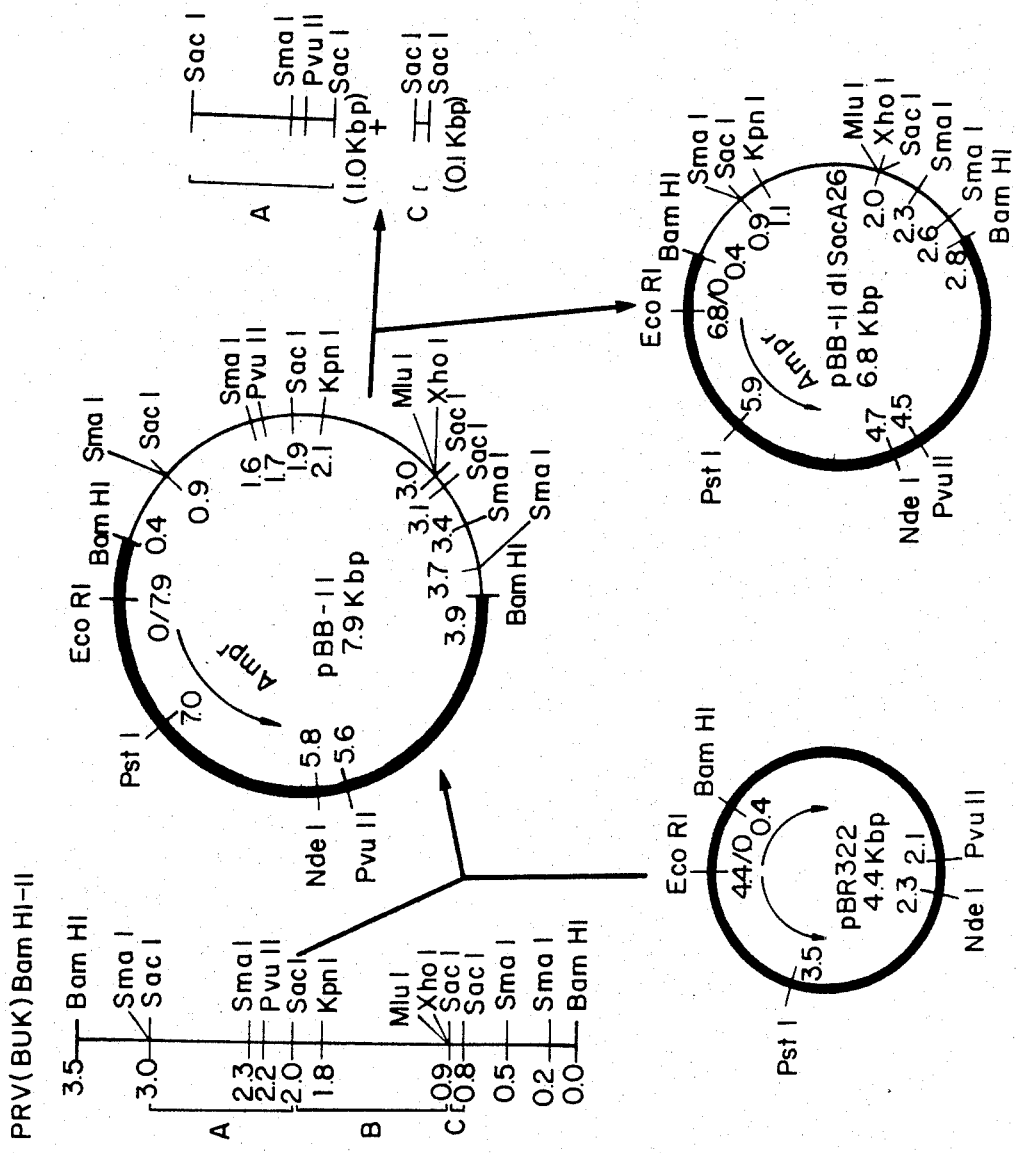
FIG. 4 schematically illustrates, by example, the derivation of the plasmids employed in the present invention. Insertion of the BamHI-11 fragment of PRV(BUK-7) into pBR322 produces hybrid plasmid pBB-11. Plasmid pBB-11 dl SacA26 is obtained by deleting the 1.0 kb SacI-A fragment and the 0.1 kb SacI-C fragment from pBB-11.

The restriction nuclease map of plasmid pBB-11, which contains a 3.5 kb BamHI fragment of PRV(BUK-7), i.e. BamHI-11, inserted at the BamHI cleavage site of pBR322, is shown in FIG. 4. This fragment contains the PRV tk gene as demonstrated by the marker transfer assay described above. To delimit the approximate boundaries of the PRV tk gene, marker transfer assays utilizing portions of the 3.5 kb BamHI fragment were carried out as described above. These experiments demonstrated that the sequences of the SacI-B fragment were essential for marker transfer of a wild-type tk$^+$ sequence to PRV(BUK-5A), but that the sequences of the SacI-A fragment of pBB-11 were not needed for marker transfer of a wild-type tk$^+$ sequence to PRV(BUK-5A) (see FIG. 4). It has also been found that 6.3 kb KpnI-J$_L$ fragment of PRV(BUK-7) (see Table 1 and FIG. 2) rescued the tk$^-$ mutation of PRV(BUK-5A). This demonstrates that the mutation in PRV(BUK-5A), and thus the coding region of the tk gene, is located between the KpnI restriction site (2.1 map units) and the BamHI restriction site (3.9 map units) of pBB-11 (see FIG. 4).

D. Nucleotide Sequence of PRV tk Gene

Portions of the 3.5 kb BamHI fragment of pBB-11 were subcloned in phages M13 mp8 to mp11 in order to sequence the PRV tk gene as described below (see: Hu, N.-T. and Messing, J. *Gene* 17:271-277 (1982); and Messing, J. and Vieira, J. *Gene* 19:269-276 (1982)).

A series of phage M13 derivatives containing a semi-synthetic lac sequence and suitable cloning sites has been designed (see: Messing, J. *Genetic Engineering* Eds. R. Setlow and A. Hollander (Plenum Publishing Corporation: New York, N.Y.) Vol. 4:19-35 (1982)). These derivatives allow the cloning of small DNA fragments in a nonessential region of phage M13 and the detection of inserts by a simple color test. The system has found broad application in DNA sequencing reactions and the preparation of DNA probes.

When fragments of the PRV tk gene are subcloned in the replicative form (hereinafter "RF") of phage M13 derivatives such as M13 mp8, M13 mp9, M13 mp10, and M13 mp11 (New England BioLabs, Inc.), the same fragment can be cloned in both possible orientations. Replication of the recombinant phage M13 derivatives leads to synthesis of single-stranded phage DNA. An M13 pentadecamer primer was used to initiate the sequencing of the single-stranded DNA (New England BioLabs, Inc. or P. L. Biochemicals).

To prepare the RF M13 derivative, 1.0 ml from an overnight culture of *E. coli* K12 JM103 bacteria (New England BioLabs, Inc. or P. L. Biochemicals) were infected with $10^7$ p.f.u. M13 mp10. After mixing with 9.0 ml of ML broth, the infected cultures were incubated for 3 hr at 37° C. One ml of the infected cultures and 9.0 ml of noninfected bacteria were then added to 0.1 liter of ML broth and the cultures were incubated at 37° C. for 7 hr more. Cultures were harvested by centrifugation, suspended in lysozyme solution No. 1, and the RF M13 mp10 DNA was extracted and purified by 10-40% (w/v) sucrose gradient and 57% (w/v) CsCl gradient centrifugation in TE buffer as described above.

SacI fragments A, B and C of the PRV tk gene, i.e., SacI fragments of PRV(BUK) BamHI-11 (see FIG. 4) were subcloned in M13 in the following manner. About 1.0 μg of pBB-11 DNA was mixed with 100 ng of RF M13 mp10 DNA, and the mixture was cleaved with 10 units of SacI (New England BioLabs, Inc.) in 6.0 mM Tris-HCl, pH 7.4, 6.0 mM MgCl$_2$, 6.0 mM 2-mercaptoethanol, and 100 μg/ml of BSA at 37° C. for 1 hr. The reaction was terminated by adding EDTA to 20 mM and by heating at 65° C. for 20 min. The reaction products were then precipitated with ethanol, dissolved in ligation buffer and ligated with 1000 units of phage T4 DNA ligase (New England BioLabs, Inc.). Next, the reaction mixture was incubated at 16° C. for 4 hr and the reaction was terminated by adding 4 volumes of TE buffer and heating at 65° C. for 10 min.

To select for recombinant M13 with PRV SacI fragment DNA inserts, 0.2 ml of CaCl$_2$-treated *E. coli* K12 JM103 bacteria, prepared as described above, were mixed with 10-50 μl of the ligated M13 mp10 DNAs and kept in an ice bath for 40 min. The mixtures were then incubated at 37° C. for 5 min with 10 μl of 100 mM isopropyl-β-D-thiogalactopyranoside and 50 μl of 2.0% (w/v) bromo-4-chloro-3-indolyl-β-D-galactopyranoside in 50% (v/v) dimethylformamide. Next, 0.2 ml of freshly growing bacteria and 3.0 ml of soft agar comprising 5.0 g yeast extract; 5.0 g NaCl; and 6.0 g bactoagar in one liter were added. The mixture was poured onto 60 mm Petri dishes and incubated at 37° C. overnight.

Thereafter, colorless plaques consisting of phage-infected bacteria were picked and inoculated into 0.2 ml of ML broth in a microtiter plate and incubated at 37° C. for 3 hr. Then, 0.2 ml of freshly growing *E. coli* K12 JM103 was added to the phage-infected bacteria; the mixtures were transferred to test tubes containing 5.0 ml of ML broth and incubated overnight at 37° C.

Next, 1.0 ml of infected bacteria was centrifuged, the supernatant was transferred to another tube, 0.5 ml of a solution containing 12% (w/v) polyethylene glycol (6000) and 1.5 mM NaCl was added, the suspension was kept at 4° C. for 10 min, and then centrifuged. The supernatant was discarded and the precipitated phage were dissolved in 0.1 ml of 0.2% (w/v) sodium dodecylsulfate, 0.25 mM EDTA. Phage DNA was then analyzed by agarose gel electrophoresis as described above. Recombinant phage were recognized by the slower mobility, i.e., larger size, of the single-stranded phage DNA containing inserts compared with single-stranded phage DNA without inserts.

To learn whether two inserts in phage M13 mp10 were complementary, the complementary test, i.e. C-test was used as described below.

More specifically, two candidate recombinant single-stranded M13 mp10 phage were mixed in 6X a buffer comprising 0.15M NaCl, 0.015M sodium citrate, pH 7.0 (hereinafter "SSC"), at 65° C. for 1 hr. Then, portions of the reaction mixture were analyzed by agarose gel electrophoresis as described above. If the two insertion sequences were complementary, they hybridized to each other and formed a slower moving band during electrophoresis than the original single-stranded phase DNAs.

Cloned SacI fragments isolated from the RF form of M13 mp10 recombinant DNA, as described above, were further cleaved by MspI or TaqI (New England BioLabs, Inc.) and cloned at the AccI site of M13 mp9 essentially as described above for subcloning SacI fragments. The RF DNA of M13 mp10 containing the PRV(BUK) BamHI 11-SacI-B fragment was also cleaved by KpnI, i.e., a cleavage site within PRV(BUK) BamHI-11 SacI-B fragment; and by SmaI, i.e., a cleavage site 3' to the cloning site in M13 mp10. The cohesive end of KpnI was converted to a blunt end using the 3' exonuclease activity of phage T4 DNA polymerase (Bethesda Research Laboratories) as described below.

In the presence of all four deoxyribonucleoside triphosphates, T4 DNA polymerase will remove unpaired 3' tails from restriction fragments and will stop when it reaches the first paired base if the appropriate complementary dNTP is present. To convert the KpnI cohesive end to a blunt end, the reaction mixture comprised 10 μl of the DNA fragment contain 1.0 μg of DNA, 2.0 μl of 10 times T4 DNA polymerase buffer, 1.0 μl of a 2.0 mM solution of all four deoxyribonucleoside triphosphates, 1.0 μl of T4 DNA polymerase, about 2.5 units, and 19 μl of water. The 10 times T4 DNA polymerase buffer comprised 0.33M Tris-acetate (pH 7.9), 0.66M potassium acetate, 0.10M magnesium acetate, 5.0 mM dithiotreitol, and 1.0 mg/ml BSA (Pentax Fraction V). The reaction mixture was incubated for 5 min at 37° C. Then, 1.0 μl of 0.5M EDTA was added to stop the reaction. The solution was extracted once with a phenol/chloroform (1:1) (v/v) solution, and the DNA was precipitated with 2 volumes of ethanol. The DNA was collected by centrifugation, washed with 70% (w/v) ethanol, recentrifuged, and dried in vacuo. The DNA was dissolved in 20 μl of TE buffer (pH 7.6), and then the blunt-ended DNA fragment was religated to the SmaI-cleavage site of the M13 mp10 fragment, eliminating the 0.8 kb or 0.2 kb KpnI/SmaI sequence, depending on the orientation (see FIG. 4).

In addition to SacI fragments of the PRV tk gene, three SmaI fragments were subcloned in phage M13 mp8 in the same manner as employed to subclone the SacI fragments described above (see FIG. 4).

To prepare single-stranded phage DNA for sequencing, 1.0 ml of phage-infected *E. coli* K12 JM103 and 1.0 ml of freshly growing uninfected bacteria were inoculated into 100 ml of ML broth and incubated for 7 hr at 37° C. Phage were precipitated from the supernatant with 12% (w/v) polyethylene glycol (6000) and 1.5 mM NaCl, collected by centrifugation, suspended in 5.0 ml of TE buffer plus 0.1 ml of 10% (w/v) sodium dodecylsulfate and 5.0 ml of 90% (v/v) aqueous phenol. The mixture was centrifuged and the aqueous phase was extracted once with 5.0 ml of phenol:chloroform (1:1). Next, the DNA was precipitated with two volumes of ethanol, and the precipitates were rinsed with 70% (v/v) and then 100% ethanol, dried in vacuo, and dissolved in 0.2 ml of TE buffer.

DNA sequencing was carried out by the dideoxynucleotide chain termination method, using single-stranded M13 mp10 subclones of PRV(BUK) BamHI-11 DNA as templates, a pentadecamer-synthetic primer (New England BioLabs, Inc.), [α-$^{32}$P]-dTTP as the labeled substrate, Mg$^{++}$, the appropriate unlabeled deoxyribonucleoside triphosphates and dideoxyribonucleoside triphosphates, and *E. coli* DNA polymerase (Klenow fragment, Bethesda Research Laboratories). After incubating the reaction mixture for 15 min at 38° C., a chase solution containing deoxyribonucleoside triphosphates was added. The reaction was terminated after 10 min at 38° C. by adding an EDTA solution containing yeast tRNA (Sigma Chemical Co.), the reaction products were precipitated with ethanol, dissolved in 10 μl of a solution comprising 90% (v/v) formamide, 30 mM NaOH, 10 mM EDTA, 0.3% (w/v) bromophenol blue, and 0.3% (w/v) xylene cyanol, heated for 1 min at 90° C., and loaded into 8.0% sequencing gels comprising 7.6% (w/v) acrylamide, 0.4% (w/v) bisacrylamide, 0.003% (v/v) TEMED, 0.007% (w/v) ammonium persulfate and 7.0% (v/v) formamide (see: Sanger, F., Coulson, A. R., Barrell, B. G., Smith, A. J. H. and Roe, B. A. *J. Mol. Biol.* 143:161–178 (1980) and Sanger, F., Nicklen, S. and Coulson, A. R. *Proc. Nat. Acad. Sci. USA* 74:5436–5467 (1977)).

The nucleotide sequence of a 1686 bp DNA fragment containing the coding region of the PRV tk gene is substantially as shown in FIG. 5. Although the nucleotide sequence shown in FIG. 5 was obtained by sequencing the tk gene of PRV(BUK-7), due to the highly evolutionary conservatism of the tk gene, other PRV tk+ strains, as exemplified above, would be expected to have tk genes with substantially similar nucleotide sequences and thus, as discussed below, the nucleotide sequence in FIG. 5 can be employed to construct additional PRV tk− deletion mutants employing PRV tk+ strains other than PRV(BUK) as the starting material.

In FIG. 5, the BamHI site (GGATCC) corresponding to the BamHI site at 3.9 map units of pBB-11 (see FIG. 4) begins at nucleotide 318. The nucleotides 5' to the BamHI site are in the BamHI-9 fragment which is adjacent to the BamHI-11 fragment of PRV DNA (see FIG. 2). The sequence then extends counterclockwise from the BamHI site of pBB-11 (3.9 map units; see FIG. 4) for 1368 nucleotides. A putative translational start signal, i.e. ATG, for the PRV TK is at nucleotide 122.

A putative translational stop signal, i.e. TGA, for the PRV TK is at nucleotide 1229. A putative transcriptional polyadenylation signal, i.e. AATAAA, for the PRV TK is at nucleotide 1411. Thus, the molecular weight of the PRV TK predicted from the sequence in FIG. 5 is 40,610 daltons. This is similar to the molecular weight of other alpha herpesvirus TKs.

Restriction nuclease sites for over 50 different restriction nucleases are predicted from the nucleotide sequence shown in FIG. 5. For example, SacI sites are predicted from the sequence at nucleotides 115, 925, 1007, 1034 and 1073, so that the SacI-C fragment deleted in pBB-11 dl SacA26, see below, would be 148 bp long, i.e. from nucleotide 925 to 1073. It should be noted that this deletion also changes the translational reading frame since the deletion is not divisible by three, i.e. a codon contains three nucleotides. Further, SmaI sites are predicted at nucleotides 4, 402 and 763 and XhoI and MluI sites are predicted at nucleotides 1100 and 1110, respectively. These predictions are consistent with the restriction nuclease map of pBB-11 (see FIG. 4) and provide precise data on sites that are close together for engineering other deletion mutants. In addition, two sites are predicted for XmaIII, three sites are predicted for BglI and HincII, and five sites are predicted for SacII. These restriction sites can be employed to construct alternative hybrid plasmids and thus other tk⁻ deletion mutants of the present invention.

E. Construction of pBB-11 Deletion Plasmids

As stated above, for specificity and high efficiency engineering of recombinant tk⁻ deletion mutants of PRV, a plasmid is required with a deletion in the coding region of the tk gene, yet containing at least 400 bp of PRV nucleotide sequences on both the 5' and 3' sides adjacent to the deletion to facilitate homologous recombination with the tk gene of PRV tk⁺ DNA. In order to construct a plasmid with these properties, plasmid pBB-11 was digested with restriction nuclease SacI, and then religated using phage T4 DNA ligase as described above (see FIG. 4).

E. coli K12 strain RR1 was then transformed with the resulting plasmids, as described above, and the plasmid DNA produced was isolated as described above. The DNAs of candidate deletion plasmids were then analyzed by agarose gel electrophoresis as described above. A plasmid, designated pBB-11 dl SacA26, was isolated which contained a deletion of SacI fragments of pBB-11, i.e. containing a deletion of the PRV(BUK) BamHI-11 SacI-A and SacI-C fragments (see FIG. 4). The restriction map of pBB-11 dl SacA26 is shown in FIG. 4. It should be again noted that SacI-C fragment contains part of the coding region of the tk gene, while the SacI-A fragment, which is downstream from the SacI-B fragment, does not contain any of the PRV tk gene. The SacI-A fragment most likely encodes a PRV gene other than the tk gene (see FIG. 4).

F. The Construction of Recombinant tk⁻ Deletion Mutant of PRV(BUK-5A-R1)

It was shown above that homologous recombination between the intact DNA of a PRV tk⁻, i.e. PRV(BUK-5A), and a hybrid plasmid containing the coding region of the PRV tk gene, i.e. pBB-11, results in the rescue of a functional tk⁺ gene in the revertant virus designated PRV(BUK-5A-R-1).

In order to obtain, by homologous recombination, a PRV deletion mutant in the tk gene, it is necessary to start with the intact DNA of a PRV tk⁺ and a hybrid plasmid containing a deletion in the coding region of the tk gene. The progeny viruses obtained following this type of cross mainly comprise parental PRV tk⁺. Thus, in order to enrich for the PRV tk⁻ in the harvests, selective media containing araT is employed, since araT inhibits PRV tk⁺ replication and favors the outgrowth of tk⁻ virus.

The hybrid plasmid chosen for this construction of the tk⁻ deletion mutant of PRV was pBB-11 dl SacA26. The PRV tk⁺ chosen for the recombination step was PRV(BUK-5A-R1).

Since the data in Table 6 below demonstrates that PRV (BUK-5A) is considerably less virulent than parental PRV(BUK-5), and that revertant PRV(BUK-5A-R1) has an intermediate virulence, which is the consequence of the mutagenesis and selection steps described above, PRV(BUK-5A-R1) DNA was preferable to PRV(BUK-5) DNA, or to the DNAs of tk⁺ field strains of PRV for the construction of the deletion mutants.

The construction of the recombinant tk⁻ deletion mutant of PRV(BUK-5A-R1) was specifically carried out in the following manner: Rab-9 cells were seeded in 60 mm Petri dishes (0.5×10⁶ cells per dish) and incubated at 37° C. for 36 hr. Cultures were co-transfected as described above with a mixture of PRV(BUK-5A-R1) and pBB-11 dl SacA26 DNAs. The virus harvested was stored frozen at −70° C. in growth medium. Then, the virus harvest from the co-transfection was thawed, sonicated, and diluted 1:5000 in growth medium supplemented with 100 µg/ml araT.

In order to enrich for PRV tk⁻ deletion viruses, the diluted virus was passaged in confluent monolayer cultures of Rab(BU) cells in 8-ounce prescription bottles in growth medium containing 100 µg/ml araT.

After a 1 hr absorption at 37° C., the infected cell monolayers were washed three times with a solution comprising 8.0 g NaCl, 0.4 g KCl, 0.1 g glucose, and 0.02 g phenol red per liter of water (hereinafter "GKN") and then growth medium containing 100 µg/ml araT was added. After 48 hr of further incubation at 34.5° C., virus was harvested.

A second selection step and plaque purification by titration of the harvest of the first selective passage was performed in Rab(BU) cells, as described above, in the presence of 100 µg/ml araT.

In control transfections lacking deletion plasmid pBB-11 dl SacA26, spontaneous mutants resistant to araT were isolated, but at only one-fourth the frequency when co-transfecting with pBB-11 dl SacA26.

Candidate recombinant PRV with tk⁻ deletions were then picked at random from individual araT-resistant plaques, and virus pools prepared.

Four candidates, designated PRV(BUK-dl 1), PRV(BUK-dl 2), PRV(BUK-dl 3) and PRV(BUK-dl 4), were obtained. PRV(BUK-dl 3) has been deposited at the American Type Culture Collection under ATCC No. VR-2074.

G. Nick Translation of pBB-11 DNA to Prepare Probes For Molecular Hybridization In order to verify that deletions were present in the tk gene of the candidate deletion mutants obtained above, molecular hybridization studies were conducted using pBB-11 DNA as probe. The pBB-11 probe was obtained in the following manner.

Purified plasmid pBB-11 DNA was radioactively labeled by nick-translating in the following manner. To 25 μl of reaction mixture containing 6.0 μmol PBS, pH 7.4; 1.8 nmol dATP; 1.8 nmol dGTP; 0.1 mCi [α-$^{32}$P]-dTTP (400 Ci/mmole); 0.1 mCi [α-$^{32}$P]-dCTP (400 Ci/mmole) (Amersham Corporation), about 1.0 μg pBB-11 DNA was added. Then, 1.33 ng in 1.0 μl of DNase I (Worthington Biochemical Corporation) was added and the reaction mixture was allowed to stand for 1 min at room temperature. Next, the reaction mixture was incubated at 14° C. with 5.0 units in 1.0 μl of E. coli DNA polymerase I (Boehringer-Mannheim Biochemicals). When the specific activity became higher than $2 \times 10^8$ cpm/μg DNA, i.e., about 3 hr, the reaction was terminated by adding 10 μl of 0.25M EDTA (pH 7.4) and heating at 68° C. for 10 min. Then, as carrier, 50 μl of a solution comprising 5.0 mg/ml sonicated salmon sperm DNA in TE buffer, was added to the mixture and the nick-translated DNA was purified by Sephadex G50 (fine) column chromatography using 10 mM NaCl, 10 mM Tris-HCl, pH 7.5, 2.0 mM EDTA as the elution buffer.

The resulting [$^{32}$P]-labeled, nick-translated DNA was used as a probe in DNA-DNA hybridization experiments after boiling in a water bath for 20 min, and quickly cooling on ice to form single-stranded DNA (see: Rigby, P. W. J., Dieckmann, M., Rhodes, G., and Berg, P. *J. Mol. Biol.* 113:237–251 (1977)).

H. Hybridization of PRV DNA with pBB-11 DNA 0.6 μg of DNA from each of strains PRV(BUK-5A-R1), PRV(BUK-dl 1), PRV(BUK-dl 2), PRV(BUK-dl 3), and PRV(BUK-dl 4) were cleaved with restriction nucleases, SmaI (New England BioLabs, Inc.), SstI (an isoschizomer of SacI) (Bethesda Research Laboratories, Inc.) and BamHI under conditions specified by the enzyme suppliers, and the fragments were separated by electrophoresis on 0.6% (w/v) agarose at 35 volts (constant voltage) for 16 hr at 4° C. The electrophoresis buffer comprised 0.04M Trizma base, 0.03M NaH$_2$PO$_4$ pH 8.1 and 0.001M EDTA. ClaI-cleaved plasmids, pMAR4 (13.6 kb), pMH110 (4.4 kb), and pAGO (6.4 kb), HindIII fragments of phage lambda DNA, and HaeIII fragments of phage ΦX174 RF DNA were also electrophoresed as markers. The results are shown in FIGS. 6A and 6B. Lanes 1, 6, and 11: PRV(BUK-dl 4); lanes 2, 7, and 12: PRV(BUK-dl 3); lanes 3, 8, and 13: PRV(BUK-dl 2); lanes 4, 9, and 14: PRV(BUK-dl 1); lanes 5, 10, and 15: PRV(BUK-5A-R1); lane 16: HindIII λ and HaeIII ΦX174 fragments (New England Biolabs, Inc.); Lane 17: ClaI-cleaved plasmids pMAR4 (13.6 kb), pAGO (6.4 kb), and pMH110 (4.4 kb) marker DNAs (see: Kit, S., Qavi, H., Dubbs, D. R. and Otsuka, H *J. Med. Virol.* 12:25–36 (1983)).

As shown in FIG. 6A, three out of four candidates were found to have alterations specific to the PRV(BUK-7) BamHI fragment which contains the tk gene, i.e. lanes 11, 12 and 13. Specifically, the 3.5 kb BamHI fragment disappeared and a new fragment of about 3.3 kb appeared. This result is consistent with a deletion of the approximately 200 bp SacI-C fragments from the PRV tk gene.

After electrophoresis, the separated DNA restriction fragments in the agarose gel were transferred to nitrocellulose filters (Schleicher and Schuell) in the following manner: The agarose gel was placed in a glass baking tray containing 1.0M KOH for 30 min at room temperature and, then, in a glass baking tray containing 1.0M Tris-HCl, pH 7.0 and 0.6M NaCl for 60 min at room temperature. The treated gel was then transferred to a blot apparatus (Bethesda Research Laboratories).

A nitrocellulose filter was prewetted in water for 10 min and then in 20X SSC for 5 min. Next, the filter was placed on the gel. Using 20X SSC as the transfer fluid, blotting was allowed to proceed for about 24 hr. The adherent gel was removed from the nitrocellulose filter and the filter was rinsed with 6X SSC, dried at room temperature for several hr, and then in a vacuum desiccator at 60° C. overnight. This was followed by 2 hr of baking at 80° C. The nitrocellulose filters were removed from the desiccator and placed in Dazey seal-a-meal cooking bags (see: Southern, E. M., *J. Mol. Biol.* 98:503–513 (1975)).

The filter was first pretreated overnight at 60° C. with 50 ml of modified Denhardt's solution comprising 3X SSC, 0.02% (w/v) polyvinylpyrollidone, 0.02% (w/v) Ficoll, 0.02% (w/v) BSA, 50 μg/ml alkaline salmon sperm DNA and 10 μg/ml poly(A). The alkaline salmon sperm DNA was added from a stock solution of about 5.0 mg/ml prepared by dissolving 50 mg of salmon sperm DNA in 10 ml of 0.2N NaOH, heating at 100° C. for 20 min to denature and shear the DNA to about 0.4 kb segments, and then neutralizing with 0.2 ml of 10N HCl.

The modified Denhardt's solution was then replaced with 50 ml of hybridization buffer comprising 50% (v/v) formamide, 0.6M NaCl, 0.2M Tris-HCl, pH 8.0, 0.02M EDTA 0.1% (w/v) sodium dodecylsulfate, 50 μg/ml alkaline salmon sperm DNA, and 10 μg/ml poly(A). Next, air bubbles were squeezed out of the bag which was then sealed using an Oster Touch-a-Matic Bag Sealer and incubated at 37° C. for 1 hr on a shaker.

Thereafter, about 1.0 ml, containing about 10$^7$ cpm and 50 nanograms, of single-stranded [$^{32}$P] nick-translated pBB-11 DNA, obtained as described above, was added to the bag with a 3.0 ml syringe by piercing the side of the bag at a corner. Next, the bag was resealed and incubated at 37° C. for up to 48 hr on a shaker to allow for hybridization.

After hybridization had been accomplished, the bag was cut and the solution was decanted. The filter was then carefully removed and placed into a tray containing about 100 ml of hybridization buffer containing 50 μg/ml denatured salmon sperm DNA for the first wash only, but no poly(A) in any wash. The filter was washed for 30 min at 37° C. five times with gentle shaking. Next, the filter was washed for 30 min at 37° C. with 0.3X SSC and then with 0.1X SSC and placed on filter paper to dry overnight at room temperature.

For autoradiography, the filter was replaced on a thin piece of cardboard covered with Saran-Wrap, and exposed to Kodak X-Omat R XR2 film with an intensifying screen for periods of 5 hr to 2 days at −70° C.

As shown in FIG. 6B, the autoradiography of the gel probed with [$^{32}$P]-labeled pBB-11 revealed that PRV(BUK-dl 1) was a spontaneous tk$^-$ mutant having a restriction pattern identical to that of the parental PRV(BUK-5A R1), whereas PRV(BUK-dl 2), PRV(BUK-dl 3), and PRV(BUK-dl 4) were tk$^-$ deletion mutants. Further, FIG. 6B demonstrates that the SacI-C fragment of the tk gene had been deleted in the recombinant viruses PRV(BUK-dl 2), PRV(BUK-dl 3) and PRV(BUK-dl 4). This deletion was found to be about 100–200 bp. Specifically, the 3.5 kb BamHI fragment disappeared and a new fragment of about 3.3 kb appeared (see FIG. 6B, lanes 11–13). In addition, alterations were found in the 1.8 kb SmaI fragment of pBB- 11. Lanes 1–3 show that in the three candidate deletion mutants identified above, this 1.8 kb SmaI fragment was shortened to about 1.6 kb as expected (see FIG. 4). No differences are apparent in FIG. 6B with the SstI-treated group because of the inability of very small DNA fragments, i.e. less than 100 bp, to bind to nitrocellulose filters.

EXAMPLE 3

Analyses of PRV tk− Stocks for tk+ Revertants

To investigate whether revertants to tk+ spontaneously arose during the propagation of the PRV tk− mutants isolated by Examples 1 and 2 above, the following plaque autoradiography experiments (see: Tenser, R. B., Jones, J. C., Ressel, S. J., and Fralish, F. A. *J. Clin. Microbiol.* 17:122–127 (1983)) were carried out.

Two million Rab(BU) cells were seeded in 100 mm plastic Petri dishes in 10 ml of growth medium and incubated at 37° C. for 2–3 days until a semiconfluent monolayer was obtained. Next, the growth medium was removed and the monolayers were washed with GKN. Duplicate dishes were then infected with PRV(BUK-dl 3), PRV(BUK-5A), no virus (as a negative control), or PRV(BUK-5) (as a positive control). With each virus, the dishes were inoculated with 0.5 ml containing either $10^2$ p.f.u./dish, $10^3$ p.f.u./dish, $10^4$ p.f.u./dish, or $10^5$ p.f.u./dish. After a 1 hr adsorption period at 37° C., 10 ml of a solution comprising 0.5% (w/v) methyl cellulose dissolved in growth medium was added and incubation was continued for 3 days at 34.5° C. Then, the methyl cellulose solution was removed with a capillary pipette and replaced with 5.0 ml of growth medium. Thereafter, [$^{14}$C]-thymidine (3.0 μCi/dish) was added for 6 hr to label the DNA.

Next, the growth medium was removed, the monolayers were washed with GKN containing 10 μg/ml of non-radioactive thymidine, and the cells were fixed by adding 15 ml of ethanol for 5 min at 23° C. Then, the cells were stained with 5.0 ml of a 0.1% (w/v) crystal violet solution for 5 min at room temperature, washed with excess tap water, and dried in air overnight. The bottoms of the Petri dishes containing the fixed cells were then placed in contact with Fuji RX X-ray film for 1 week. Upon developing the film, the PRV tk+ plaques appeared as circles with dark rims due to isotope incorporation, whereas tk− plaques were unlabeled, i.e. no dark rims. The results demonstrated that the plaques obtained from the progeny of PRV(BUK-5A-R1) infections were heavily labeled and, therefore, of the tk+ phenotype. In contrast, the plaques obtained from the progeny of PRV(BUK-5A) and PRV(BUK-dl 3) were unlabeled and, therefore, of the tk− phenotype. Thus, reversion of PRV tk− to PRV tk+ was not detected, i.e. the spontaneous reversion rate for PRV(BUK-5A) and PRV(BUK-dl 3) is less than $10^{-5}$.

EXAMPLE 4

TK Activity of PRV Strains

TK activity of various PRV strains was assayed in the following manner. Cytosol extracts were prepared from about $10^8$ mock-infected or PRV-infected Rab(BU) cells at 6 hr post infection by Dounce homogenization of cell pellets suspended in 5 volumes of hypotonic buffer comprising 0.01M KCl, 0.0015M MgCl$_2$, and 0.01M Tris-HCl, pH 7.4. Then, 1/9 volume of a solution containing 1.5M KCl, 0.03M 2-mercaptoethanol, 25% (v/v) glycerol, and 0.5M epsilon aminocaproic acid was added to adjust the KCl concentration to isotonicity and to stabilize the enzyme. The homogenate was centrifuged for 1 hr at 4° C. in a Spinco No. 65 rotor at 40,000 rpm and the supernatant was transferred to vials. Aliquots were taken for determination of the protein concentration and for TK activity assays.

TK assays were performed at three different enzyme levels, e.g., 75, 113, and 188 μg protein per assay tube, for 10 min at 38° C. under conditions standardized to insure zero order kinetics. The reaction mixture contained 0.1 mM [$^3$H]-deoxythymidine (291 cpm/picomole deoxythymidine), 2.0 mM ATP, 1.0 mM MgCl$_2$, 10 mM KF, 100 mM Tris-HCl, pH 8.0, and protein in a total volume of 0.125 ml. The reaction was terminated by the addition of 0.025 ml of 50% (w/v) trichloroacetic acid. After low speed centrifugation at 1000×g to remove precipitated proteins, 0.02 ml portions were spotted on DEAE-cellulose sheets (Whatman). The [$^3$H]-dTMP product of the reaction was separated from the substrate [$^3$H]-deoxythymidine by chromatography in solvent made by adding 175 ml of 88% formic acid and 6.3 g of ammonium formate to water in a total volume of one liter. The [$^3$H]-dTMP spots were visualized by UV light and were cut from the paper. Then, the radioactivity in each spot was determined by liquid scintillation spectrometry (see: Kit, S. and Qavi, H. *Virology* 130:381–389 (1983)). The results are shown in Table 3 below.

TABLE 3

Thymidine Kinase Activity of Rab(BU) Cells Infected for 6 Hr with PRV tk+ and PRV tk− Strains

| PRV strain used to infect Rab(BU) cells | TK activity |
| --- | --- |
| Mock-infected Rab(BU) | 0.09 |
| PRV(BUK-5) | 4.8 |
| PRV(BUK-5A R1) | 3.5 |
| PRV(BUK-5A) | 0.03 |
| PRV(BUK-dl 2) | 0.03 |
| PRV(BUK-dl 3) | 0.02 |
| PRV(BUK-dl 4) | 0.03 |

As Table 3 above demonstrates: (i) Rab(BU) cells, i.e. tk− cells, have negligible TK activity; (ii) TK activity is acquired by Rab(BU) cells after infection with the tk+ virus PRV(BUK-5), but not after infection with the tk− viruses PRV(BUK-5A), PRV(BUK-dl 2), PRV(BUK-dl 3) or PRV(BUK-dl 4) and (iii) TK activity is also acquired after Rab(BU) cells are infected with the tk+ virus PRV(BUK-5A-R1).

EXAMPLE 5

Virulence of PRV Strains

It is generally agreed that several genes contribute to the ability of alpha herpesviruses to cause disease, i.e., that virulence is multigenic. It is known, for example, that alpha herpesvirus strains differ in their ability to establish latency, to ascend the nervous system and to cause encephalitis, or to cause abortions in pregnant animals. As discussed above, the tk gene is one of the genes contributing to virulence, but it is not the only gene which contributes to virulence. That is, the Bucharest and Bartha strains of PRV are attenuated for swine compared to the Aujeszky strain or field isolates of PRV, but all of the above-mentioned virus strains are PRV tk+ strains. This example demonstrates that PRV(BUK) can be further attenuated by mutating the tk gene to the tk− phenotype.

The parental PRV strain utilized for the isolation of tk− viruses was, as described above, PRV(BUK), a tk+ strain previously attenuated by many passages in chick cells and found to be useful in protecting swine against Aujeszky's Disease (see: Skoda, R., Brauner, I., Sadecky, E., and Mayer, V. *Acta Virol* 8:1-9 (1964)). PRV(BUK) has also been shown to be partially attenuated for cattle, but low doses of the virus produce fatal infections in rabbits and mice. Thus, the sensitivity of the laboratory animals to PRV is an appropriate measurement of virulence of the genetically engineered PRV tk$^-$ strains of the present invention in these animals.

In order to assess the virulence of the viruses of the present invention, mice were inoculated intraperitoneally with PRV(BUK-5), PRV(BUK-5A) and PRV(BUK-5A-R1). The results are shown in Table 4 below.

TABLE 4

Mortality of 3-Week-Old Female Swiss Mice After Injection of PRV tk$^+$ and tk$^-$ Strains

| Virus Strain | Dose p.f.u./ mouse | Route[a] | Mortality No. dead/ No. injected | LD$_{50}$[b] p.f.u./ mouse |
|---|---|---|---|---|
| EXPERIMENT 1 | | | | |
| PRV(BUK-5) | $10^3$ | IP | 5/5 | 68 |
| | $10^2$ | | 3/5 | |
| | $10^1$ | | 0/5 | |
| PRV(BUK-5A-R1) | $10^5$ | IP | 5/5 | 4800 |
| | $10^4$ | | 3/5 | |
| | $10^3$ | | 1/5 | |
| | $10^2$ | | 2/5 | |
| PRV(BUK-5A) | $10^7$ | IP | 0/5 | $>10^7$ |
| | $10^6$ | | 0/5 | |
| | $10^5$ | | 0/5 | |
| EXPERIMENT 2 | | | | |
| PRV(BUK-5) | $10^4$ | SC | 4/5 | 2070 |
| | $10^3$ | | 2/5 | |
| PRV(BUK-dl 3) | $10^7$ | SC | 0/5 | $>10^7$ |
| | $10^6$ | | 0/5 | |
| | $10^5$ | | 0/5 | |

[a]IP is intraperitoneal; SC is subcutaneous.
[b]LD$_{50}$ is the lethal dose for 50% of the mice.

The results shown in Experiment 1 in Table 4 above demonstrate that, for intraperitoneal inoculation, the LD$_{50}$ value for parental PRV(BUK-5), i.e. a tk$^+$ virus, was about 68 p.f.u./mouse and that for PRV(BUK-5A), i.e. a tk$^-$ virus, the LD$_{50}$ value was greater than $10^7$. PRV(BUK-5A) has also been found to be less virulent (LD$_{50}$=500) than tk$^+$ virus PRV(BUK-5) (LD$_{50}$=2) after intracranial inoculations in mice. Further, the results in Experiment 1 in Table 4 show that PRV(BUK-5A-R1), i.e. a tk$^+$ virus, which had received a PRV tk gene from plasmid pBB-11, had an intermediate LD$_{50}$ of about 4800. This demonstrates that PRV virulence can be significantly increased by restoring a functional tk gene to PRV and that this gene is important to pathogenicity. Further, since PRV(BUK-5A-R1) had an intermediate virulence, the results demonstrate that the process of attenuating PRV in the first embodiment of the present invention, as exemplified in Example 1, introduces changes in the virus beyond those affecting the tk gene and that these changes confer enhanced attenuation. In addition, since PRV(BUK-5A-R1) was used as the substrate to produce tk− deletion mutants in Example 2, the additional attenuating mutations are retained in the PRV tk− deletion mutants.

Additional studies entailing the subcutaneous inoculation of the tk− deletion mutant, PRV(BUK-dl 3), are shown in Table 4, Experiment 2, above. Mice survived infection by the undiluted tk− deletion mutant PRV(BUK-dl 3), i.e. inoculation of 0.1 ml of virus having a titer of $10^8$ p.f.u./ml. On the other hand, $10^4$ p.f.u. of PRV(BUK-5) killed four out of five mice and $10^3$ p.f.u. killed two out of five mice.

It has also been found that after subcutaneous inoculation of 1 to 10 p.f.u. of PRV(BUK-5), a fatal infection is produced in every infected 5 to 6 pound New Zealand rabbits in 4 to 6 days. However, one out of three rabbits survive infection by $10^3$ to $10^5$ p.f.u. of PRV(BUK-5A) and PRV(BUK-dl 3). The rabbits that do not survive took longer to die, i.e. 7 to 12 days.

A further indication that PRV(BUK-dl 3) has reduced virulence comes from pilot trials in calves. That is, calves infected with virulent PRV strains develop clinical signs of infection including central nervous system signs, such as tremor, ataxia, and excitation. These signs develop after a 6 to 7 day period of incubation and the calves die within a few hours, i.e. not more than 12 hours after appearance of the signs of disease. In calves sero-negative for PRV antibodies, the $LD_{50}$ value is about $10^4$ to $10^5$ $TCID_{50}$ for virulent virus administered intranasally and slightly less for virulent virus administered intramuscularly or intradermally (see: Skoda, R., Brauner, I., Sadecky, E. and Mayer, V. *Acta Virol.* 8:1-19 (1969) and Biron, P., Vandeputte, J., Pensaert, M. B. and Leunan, *J. Am. J. Vet. Res.* 43:760-763 (1982)). One $TCID_{50}$ is equivalent to 0.7 p.f.u.

On the other hand, both a calf inoculated intramuscularly with $2\times10^7$ p.f.u. of PRV(BUK-dl 3) and a second calf inoculated intranasally with $2\times10^8$ p.f.u. of PRV(BUK-dl 3), survived infections and neither calf exhibited untoward clinical effects such as tremors, ataxia or excitation. This result demonstrates that PRV(BUK-dl 3) may also be safely employed as a vaccine in calves.

EXAMPLE 6

Resistance of Vaccinated Animals to Challenge with PRV tk+

To learn whether mice vaccinated with the PRV tk− strains were protected from the pathogenic effects of PRV tk+ strains, challenge experiments with lethal doses of tk+ viruses were performed as described below.

At about three weeks after vaccination of the mice in Example 5 by intraperitoneal or sacrolumbar infections with PRV(BUK-5A) and PRV(BUK-dl 3), respectively, the mice were infected with either PRV(BUK-5) or PRV(Auj) (see Table 5). The vaccinated mice were clearly resistant to challenge with more than 100 times the $LD_{50}$ of tk+ viruses. Of the control mice that were not vaccinated, five out of seven succumbed to intraperitoneal infection by $10^4$ p.f.u. of PRV(BUK-5), and three out of four succumbed to a subcutaneous infection by $2\times10^5$ PRV(BUK-5). However, none of the mice that had previously been vaccinated intraperitoneally with $10^6$ or $10^7$ p.f.u. of PRV(BUK-5A) died from infection by $10^4$ p.f.u. of PRV(BUK-5), and only two out of five mice vaccinated with $10^4$ or $10^5$ p.f.u. of PRV(BUK-5A) died after infection by $10^4$ p.f.u. of PRV(BUK-5).

Of the mice vaccinated subcutaneously with $10^7$ p.f.u. of PRV(BUK-dl 3), only one out of five was killed by $2\times10^6$ p.f.u. of PRV(BUK-5) and only one out of five was killed by $2\times10^5$ p.f.u. of PRV(Auj).

The above results clearly demonstrate that the PRV tk− strains of the present invention are highly protective of mice against the pathogenic effects of PRV tk+ infections.

It should be noted that mice are extremely sensitive to PRV and the challenge virus doses employed in this example were very high, i.e. $10^4$ to $2 \times 10^6$ p.f.u. In field infections, it is unlikely that swine or calves would be exposed to greater than $10^3$ to $10^4$ p.f.u. of PRV. Thus, it is believed from the above results that the vaccine viruses of the present invention would be efficacious under field conditions.

TABLE 5

Mortality of Mice on Challenge with PRV tk+ After Vaccination with PRV tk−

| Previous Inoculation | | | Challenge Dose of PRV tk+ | Mortality on Challenge With PRV tk+ |
|---|---|---|---|---|
| Virus strain | Dose (p.f.u.) | Route[a] | (p.f.u.) | No. dead/No. inoculated |
| EXPERIMENT 1 | | | | |
| None | None | — | $10^{4b}$ | 5/7 |
| PRV(BUK-5A) | $10^4$ | IP | $10^{4b}$ | 2/5 |
| PRV(BUK-5A) | $10^5$ | IP | $10^{4b}$ | 2/5 |
| PRV(BUK-5A) | $10^6$ | IP | $10^{4b}$ | 0/4 |
| PRV(BUK-5A) | $10^7$ | IP | $10^{4b}$ | 0/4 |
| EXPERIMENT 2 | | | | |
| None | None | — | $2 \times 10^{6b}$ | 3/5 |
| None | None | — | $2 \times 10^{5b}$ | 3/4 |
| PRV(BUK-dl 3) | $10^5$ | SC | $2 \times 10^{5b}$ | 1/5 |
| PRV(BUK-dl 3) | $10^6$ | SC | $2 \times 10^{5b}$ | 1/5 |
| PRV(BUK-dl 3) | $10^7$ | SC | $2 \times 10^{5b}$ | 0/5 |
| PRV(BUK-dl 3) | $10^7$ | SC | $2 \times 10^{5b}$ | 1/5 |
| PRV(BUK-dl 3) | $10^7$ | SC | $2 \times 10^{5c}$ | 1/5 |
| PRV(BUK-dl 3) | $10^7$ | SC | $2 \times 10^{6c}$ | 3/5 |

[a]IP is intraperitoneal; SC is subcutaneous in sacrolumbar region.
[b]Challenged with PRV(BUK-5).
[c]Challenged with PRV(Auj).

While the invention has been described in detail and with reference to specific embodiments thereof, it will be apparent to one skilled in the art that various changes and modifications can be made therein without departing from the spirit and scope thereof.

We claim:

1. A temperature-resistant pseudorabies virus which fails to produce any functional TK as a result of mutagen-induced mutation.

2. The temperature-resistant pseudorabies virus which fails to produce any functional TK as in claim 1, wherein said virus has the identifying characteristics of PRV(BUK-5A) (ATCC No. VR-2078).

3. The temperature-resistant pseudorabies virus which fails to produce any functional TK as in claim 1, wherein said virus is lypholized.

4. A temperature-resistant pseudorabies virus which fails to produce any functional TK as a result of mutagen-induced mutation produced by a process comprising:

(1) plaque-purifying a PRV tk+ strain in tk− host cells at a permissive temperature for a temperature-sensitive virus;

(2) propagating the resulting virus of step (1) in tk− host cells 2 to 5 times in the presence of a mutagen at a permissive temperature for a temperature-sensitive virus;

(3) propagating the resulting virus of step (2) in tk+ host cells in the presence of a mutagen at a non-permissive temperature for a temperature-sensitive virus;

(4) propagating the resulting virus of step (3) in tk+ host cells in the presence of a mutagen at a permissive temperature for a temperature-sensitive virus;

(5) propagating the resulting virus of step (4) in tk+ host cells in the presence of a selective agent at a permissive temperature for a temperature-sensitive virus; and (6) propagating the resulting virus of step (5) in tk+ host cells in the presence of a mutagen at a permissive temperature for a temperature-sensitive virus to produce a temperature-resistant PRV tk− mutagen-induced mutant.

5. The temperature-resistant pseudorabies virus which fails to produce any functional TK as in claim 4, wherein said virus has the characteristics of PRV(BUK-5A) (ATCC No. VR-2078).

6. The temperature-resistant pseudorabies virus which fails to produce any functional TK as in claim 4, wherein said virus is lypholized.

7. The temperature-resistant pseudorabies virus which fails to produce any functional TK as in claim 4, wherein said PRV tk+ strain is selected from the group consisting of PRV(BUK) strain, SUCH-1 strain, K strain, Norden strain, PRV(Auj) strain, P-2208 strain, KC-152D strain, S62/26 Iowa strain, IND-FH strain, IND-S strain, IND-R strain and Shope strain.

8. The temperature-resistant pseudorabies virus which fails to produce any functional TK as in claim 7, wherein said PRV tk+ strain is PRV(BUK) strain.

9. The temperature-resistant pseudorabies virus which fails to produce any functional TK as in claim 4, wherein said permissive temperature for a temperature-sensitive virus is about 33° to 37.5° C.

10. The temperature-resistant pseudorabies virus which fails to produce any functional TK as in claim 9, wherein said permissible temperature for a temperature-sensitive virus is 34.5° C.

11. The temperature-resistant pseudorabies virus which fails to produce any functional TK as in claim 4, wherein said non-permissive temperature for a temperature-sensitive virus is about 38.5° to 40° C.

12. The temperature-resistant pseudorabies virus which fails to produce any functional TK as in claim 11, wherein said non-permissive temperature for a temperature-sensitive virus is 39.1° C.

13. The temperature-resistant pseudorabies virus which fails to produce any functional TK as in claim 4, wherein said tk− host cells are selected from the group consisting of rabbit Rab(BU), mouse LM(TK−), human HeLa(BU25), syrian hamster BHK 21 (TK−) and human line 143.

14. The temperature-resistant pseudorabies virus which fails to produce any functional TK as in claim 13, wherein said tk⁻ host cells are rabbit Rab(BU).

15. The temperature-resistant pseudorabies virus which fails to produce any functional TK as in claim 4, wherein said tk+ host cells are selected from the group consisting of Rab-9, primary rabbit kidney cells, secondary rabbit kidney cells, monkey cells, human cells, human embryonic kidney cells and chick embryo fibroblast cells.

16. The temperature-resistant pseudorabies virus which fails to produce any functional TK as in claim 15, wherein said tk+ host cells are Rab-9.

17. The temperature-resistant pseudorabies virus which fails to produce any functional TK as in claim 4, wherein said mutagen is selected from the group consisting of BrdUrd, NH₂OH, HONO, nitrosoguanidine and UV light.

18. The temperature-resistant pseudorabies virus which fails to produce any functional TK as in claim 17, wherein said mutagen is BrdUrd.

19. The temperature-resistant pseudorabies virus which fails to produce any functional TK as in claim 4, wherein said selective agent is selected from the group consisting of BrdUrd, araT, BVDU, FMAU and AIdUrd.

20. The temperature-resistant pseudorabies virus which fails to produce any functional TK as in claim 19, wherein said selective agent is araT.

21. A temperature-resistant pseudorabies virus which fails to produce any functional TK as a result of a deletion in the tk gene.

22. The temperature-resistant pseudorabies virus which fails to produce any functional TK as in claim 21, wherein said deletion is about 10 to 1500 bp in size.

23. The temperature-resistant pseudorabies virus which fails to produce any functional TK as in claim 22, wherein said deletion is about 75 to 750 bp in size.

24. The temperature-resistant pseudorabies virus which fails to produce any functional TK as in claim 21, wherein said virus has the identifying characteristics of PRV(BUK-dl 3) (ATCC No. VR-2074).

25. The temperature-resistant pseudorabies virus which fails to produce any functional TK as in claim 102, wherein said virus is lypholized.

26. A temperature-resistant pseudorabies virus which fails to produce any functional TK as a result of a deletion in the tk gene produced by a process comprising:
(1) constructing a hybrid plasmid comprising a cloning vector and a DNA fragment of PRV containing substantially all of the PRV tk gene;
(2) co-transfecting, in tk+ host cells, the hydrid plasmid of step (1) with DNA from a temperature-resistant PRV tk⁻ mutagen-induced mutant;
(3) selecting, in tk⁻ host cells, for PRV tk+ from the virus produced in step (2);
(4) deleting DNA sequences from the hydrid plasmid of step (1) such that less than substantially all of the PRV tk gene is present, while retaining PRV DNA sequences adjacent to each side of the deletion;
(5) co-transfecting, in tk+ host cells, PRV tk+ DNA derived from the PRV tk+ obtained in step (3) with the resulting hybrid plasmid of step (4); and
(6) selecting, in tk⁻ host cells, for PRV tk⁻ from the virus produced in step (5) to produce temperature-resistant PRV tk⁻ deletion mutants.

27. The temperature-resistant pseudorabies virus which fails to produce any functional TK as in claim 26, wherein said deletion is about 10 to 1500 bp in size.

28. The temperature-resistant pseudorabies virus which fails to produce any functional TK as in claim 27, wherein said deletion is about 75 to 750 bp in size.

29. The temperature-resistant pseudorabies virus which fails to produce any functional TK as in claim 26, wherein said virus is PRV (BUK-dl 3) (ATCC No. VR-2074).

30. The temperature-resistant pseudorabies virus which fails to produce any functional TK as in claim 26, wherein said virus is lypholized.

31. The temperature-resistant pseudorabies virus which fails to produce any functional TK as in claim 26, wherein said cloning vector is selected from the group consisting of pBR322, pMB9, pBR325, pKH47, pBR328, pHC79, phage Charon 28, pKB11, pKSV-10, pMAR420 and oligo (dG)-tailed pBR322.

32. The temperature-resistant pseudorabies virus which fails to produce any functional TK as in claim 31, wherein said cloning vector is pBR322.

33. The temperature-resistant pseudorabies virus which fails to produce any functional TK as in claim 26, wherein said hybrid plasmid of step (1) is pBB-11.

34. The temperature-resistant pseudorabies virus which fails to produce any functional TK as in claim 26, wherein the PRV DNA sequences adjacent to each side of the deletion are at least about 400 bp in size.

35. The temperature-resistant pseudorabies virus which fails to produce any functional TK as in claim 26, wherein the resulting hybrid plasmid of step (4) is pBB-11 dl SacA26.

36. The temperature-resistant pseudorabies virus which fails to produce any functional TK as in claim 26, wherein said temperature-resistant PRV tk⁻ mutagen-induced mutant is PRV(BUK-5A) (ATCC No. VR-2078).

37. The temperature-resistant pseudorabies virus which fails to produce any functional TK as in claim 26, wherein said PRV tk+ DNA of step (5) is derived from PRV(BUK-5A-R1).

38. The temperature-resistant pseudorabies virus as in claim 26, wherein said tk+ host cells are selected from the group consisting of Rab-9, primary rabbit kidney cells, secondary kidney cells, monkey cells, human cells, human embrynoic kidney cells and chick embryo fibroblast cells.

39. The temperature-resistant pseudorabies virus as in claim 38, wherein said tk+ host cells are Rab-9.

* * * * *

UNITED STATES PATENT AND TRADEMARK OFFICE
CERTIFICATE OF CORRECTION

PATENT NO. : 4,514,497
DATED : April 30, 1985
INVENTOR(S) : Malon Kit, et al

It is certified that error appears in the above-indentified patent and that said Letters Patent is hereby corrected as shown below:

Column 1, line 3 insert

-- The invention described herein was developed during the tenure of a Research Career Award to Saul Kit from the United States Public Health Service of Department of Health and Human Services. The Government has certain rights. --

Signed and Sealed this

Fourth Day of April, 1995

*Attest:*

BRUCE LEHMAN

*Attesting Officer*     *Commissioner of Patents and Trademarks*

US004514497B1

REEXAMINATION CERTIFICATE (3443rd)

United States Patent [19]

Kit et al.

[11] B1 4,514,497

[45] Certificate Issued Feb. 24, 1998

[54] MODIFIED LIVE PSEUDORABIES VIRUSES

[75] Inventors: Malon Kit; Saul Kit, both of Houston, Tex.

[73] Assignee: Novagene, Inc., Houston, Tex.

Reexamination Requests:
No. 90/004,014, Nov. 1, 1995
No. 90/004,326, Aug. 7, 1996

Reexamination Certificate for:
Patent No.: 4,514,497
Issued: Apr. 30, 1985
Appl. No.: 567,018
Filed: Dec. 30, 1983

Certificate of Correction issued Apr. 4, 1995.

[51] Int. Cl.$^6$ .................. C12N 7/00; A61K 39/205; A61K 39/245
[52] U.S. Cl. .................. 435/235.1; 424/205.1; 424/229.1; 424/822; 435/172.1; 435/172.3; 435/236; 536/23.72
[58] Field of Search .................. 435/235.1, 172.1, 435/172.3, 236; 424/205.1, 229.1, 822; 536/23.72

[56] References Cited

U.S. PATENT DOCUMENTS

| | | | |
|---|---|---|---|
| Re. 33,772 | 12/1991 | Berns et al. | |
| 4,049,794 | 9/1977 | Straub | |
| 4,070,453 | 1/1978 | Bordt et al. | |
| 4,514,497 | 4/1985 | Kit et al. | 435/235.1 |
| 4,569,841 | 2/1986 | Kit | |
| 4,609,548 | 9/1986 | Kit et al. | 424/229.1 |
| 4,680,176 | 7/1987 | Berns et al. | |
| 4,694,071 | 9/1987 | Almond et al. | |
| 4,703,011 | 10/1987 | Kit et al. | |
| 4,769,331 | 9/1988 | Roizman et al. | 435/172.3 |
| 4,877,737 | 10/1989 | Shih et al. | |
| 4,999,296 | 3/1991 | Kit et al. | |
| 5,028,426 | 7/1991 | Berns et al. | |

FOREIGN PATENT DOCUMENTS

| | | | |
|---|---|---|---|
| 074808 | 3/1983 | European Pat. Off. | C12N 15/00 |
| 0141458 | 5/1985 | European Pat. Off. | |
| 0162738 | 11/1986 | European Pat. Off. | |
| 0256677 | 2/1988 | European Pat. Off. | |
| 0149040 | 6/1993 | European Pat. Off. | |
| 2356726 | 1/1978 | France | |
| WO 8704075 | 7/1987 | WIPO | |

OTHER PUBLICATIONS

Aronson, *Veterinary Pharmaceutical & Biologicals*, Harwal Publishing Co., pp. 15/119–120 (1980–1981).
Arrand et al, *J. Gen. Virol.*, 41:573–586 (1978).
Bachenheimer et al, *J. Virol.*, 10(4):875–879 (1972).
Balasubramamiam et al., *J. Gen. Virology*, 71:2979–2987 (1990).
Bankier et al, *Mo. Biol. Med.*, 1:21–45 (1983).
Bartha, *Acta Vet. Acad. Sci. Hum.*, Tomus, 19:97–99 (1969).
Bartkoski et al, *J. Virol.*, 20(3):583–588 (1976).
Batterson et al, *Virol.*, 46:371–377 (1983).
Beck et al, *BioTechniques*, 14(3):375 (1993).
Bello et al, *J. Virol.*, 189:407–414 (1992).
Bello et al, *J. Virol.*, 61:4023–4025 (1987).
Ben–Porat et al, *Virol.*, 122:251–267 (1982).
Ben–Porat et al, *Virol.*, 132:303–314 (1984).
Ben–Porat et al, *CEC Prog. of Coordination of Research on Animal, Pathology*, Federal Republic of Germany, Sep. 21–24 (1982).
Ben–Porat et al, *Mol. Bio. of Pseudorabies Virus*, Plenum Press, Ch. 3, pp. 105–107 (1985).
Ben–Porat et al, *Virol.*, 127:194–204 (1983).
Berget et al, *Proc. Natl. Acad. Sci., USA*, 74(8):3171–3175 (1977).
Berk et al, *Proc. Natl. Acad. Sci., USA*, 75(3):1274–1278 (1978).
Berns et al, *J. of Virol.*, 53:89–93 (1985).
Biswas et al, *Science*, 219:941–943 (1984).
Black et al, *Biochem.*, 32:11618–11626 (1993).
Bodemer et al, *J. Virol.*, 60(1):114–123 (1986).
Bodescot et al, *EMBO J.*, 3:1913–1917 (1984).
Bodon et al, *Acta Vet. Acad. Sci. Hum.*, Tomus, 18:107–109 (1968).
Campione–Piccardo et al, *J. Virol.*, 31(2)281–287 (1979).
Chatis et al, *Virol.*, 180:793–797 (1991).
Clark et al, *J. Am. Vet. Med. Ass.*, 185(12):1535–1537 (1984).
Clough et al, *Science*, 216:70–73 (1982).
Coen et al, *J. Virol.*, 49:236–247 (1984).
Coen et al, *In Virology*, 168:221–232 (1989).
Colbere–Garapin, *Proc. Natl. Acad. Sci. USA*, 76(8):3755–3759 (1979).
Cubitt et al, *Virus Res.*, 34:64–79 (1994).
Darby et al, *J. Gen. Virol.*, 67:753–758 (1986).
Darnell et al, *Science*, 202:1257–1260 (1978).
Davison et al, *Proc. Natl. Acad. Sci., USA*, 70:138–142 (1973).
Davison et al, *Gen Virol.*, 68:1067–1079 (1987).
Davidson et al, *J. Gen. Virol.*, 64:1927–1942 (1983).
Davison et al, *J. Gen. Virol.*, 55:315–331 (1981).
Dayhoff et al, *Methods Enzymol.*, 91:524–545 (1983).
De Clercq, *J. Antimicrobial Chemotherapy*, 14(Supp. A):85–95 (1984).
Donner et al, *Int. J. Cancer*, 20:256–267 (1977).
Doolittle, *Science*, 214:149–159 (1981).
Dubbs et al, *Virol.*, 22:493–502 (1964).
Dubbs et al, *Virol.*, 22:214–225 (1964).
Dubbs et al, *Virology*, 25:256–270 (1965).
Dube et al, *Biochem.*, 30:11760–11767 (1991).
Enquist et al, *Gene*, 7:335–342 (1979).
Estes et al, *J. Virol.*, 24:13–21 (1977).
*Feedstuffs*, Feb. 13, 1984.
Feldman et al, *J. Gen. Virol.*, 54:333–342 (1981).

(List continued on next page.)

*Primary Examiner*—Mary E. Mosher

[57] ABSTRACT

Temperature-resistant pseudorabies viruses which fail to produce any functional TK as a result of mutagen-induced mutation and temperature-resistant pseudorabies viruses which fail to produce any functional TK as a result of a deletion in the tk gene, vaccines containing same, methods for production of same and methods for use of same.

OTHER PUBLICATIONS

Fenner et al, *Veterinary Virology*, Academic Press, p. 275 (1987).
Fenner et al, *Medical Virology*, Academic Press, p. 232 (1976).
Field et al, *J. Hyg. Camb.*, 81:267 (1978).
Field, *Antiviral Res.*, 5:157–168 (1985).
Field et al, *Antiviral Res.*, 4:43–52 (1984).
Fiers et al, *Nature*, 273:113–120 (1978).
Fitch et al, *Proc. Natl. Acad. Sci. USA*, 80:1382–1386 (1983).
Frink et al, *J. Virol.*, 45(2):634–647 (1983).
Frink et al, *J. Virol.*, 39(2):559–572 (1981).
Fyfe et al, *Mol. Pharmacol.*, 24:316–323 (1983).
Fyfe et al, *Mol. Pharmacol.*, 21:432–437 (1982).
Gateley et al, *J. Infect. Dis.*, 161:711–715 (1990).
Gentry, *Pharmac. Ther.*, 54:319–355; 322–323 (1992).
Gentry et al, *Virol.*, 65:294–296 (1975).
Gielkens et al, *J. Gen. Virol.*, 66:69–82 (1985).
Glass, *Gene Function*, University of California Press, Ch. 3, pp. 110–112 (1982).
Gordon et al, *In Archives of Virology*, 76:39–49 (1983).
Goz et al, *Pharmacol. Rev.*, 29:249–272 (1978).
Haarr et al, *J. Virol.*, 56:512–519 (1985).
Haarr et al, *J. Gen. Virol.*, 68:2817–2879 (1987).
Hall et al, *Virol.*, 116:535–543 (1982).
Hall et al, *Virol.*, 132:26–37 (1982).
Halliburton et al, *J. Gen. Virol.*, 68:1435–1440 (1987).
Hamada et al, *Virol.*, 28:271–281 (1966).
Hanson et al, *Virol.*, 202:659–664 (1994).
Harris et al, *Proc. Natl. Acad. Sci. USA*, 77:4206–4210 (1980).
Hegenschied et al, *Acta Virol.*, 26:56–66 (1982).
Heller et al, *J. Virol.*, 44(1):311–320 (1982).
Hirano et al, *Acta Virol.*, 23:226–230 (1979).
Honess, *J. Gen. Virol.*, 65:2077–2107 (1984).
Hopwood, *Methods in Microbiology*, 3:363–433 (1970).
Huffman et al., *Anals. N.Y. Acad. Sci.*, 284:233–238 (1977).
Humphrey et al, *Texas Report on Biol. and Med.*, 23(1):321–336 (1965).
Hutchinson et al, *J. Virol.*, 8:181–189 (1971).
Huy et al, *Acta Virol.*, 21:397–404 (1977).
Ihara et al, *Virol.*, 122:268–278 (1982).
Ikura et al, *J. Virol.*, 48(2):460–471 (1983).
Inglis et al, *J. Gen. Virol.*, 68:39–46 (1987).
Instructions to Authors, *J. Virol.*, 45(1):i–ii (1983).
Izuni et al, *Microbial Pathogenesis*, 4:145–153 (1988).
Jacquemont et al, *J. Gen. Virol.*, 29:155–165 (1975).
Jamieson et al, *Virology*, 85:109–117 (1978).
Jamieson et al, *J. Gen. Virol.*, 24:465–480 (1974).
Jay et al, *Proc. Natl. Acad. Sci., USA*, 76:625–629 (1979).
Jones, *Cell*, 40:485–486 (1985).
Kaplan et al, *Virol.*, 23:90–95 (1964).
Kaplan et al, *Virol.*, 7:394–407 (1959).
Katz et al, *Biologicals*, 20:187–195 (1992).
Kaufman et al, *Virology*, 18:567–569 (1962).
Kaufman et al, *Science*, 145:585–586 (1964).
Khristova et al, *In Vet. Sci.*, XXII(3):15–22 (1985).
Kit et al, *Cancer Res.*, 18:598–602 (1958).
Kit et al, *Vir. Vac. Med. Clin. N. Amer.*, 67:1129–1145 (1983).
Kit, *Microbial. Sci.*, 2:369–374 (1985).
Kit et al, *Virol.*, 76:331–340 (1977).
Kit et al, *Progr. Med. Virol.*, 21:13–34 (1975).
Kit et al, *High Technology Route to Virus Vaccines*, Amer. Soc. for Micro., pp. 82–99 (1985).
Kit et al, *Nucl. Acids Res.*, 8:5233–5253 (1980).
Kit et al, *Biochem. Biophys. Res. Comm.*, 8:72–75 (1962).
Kit et al, *Gene*, 16:287–295 (1981).
Kit et al, *J. Med. Virol.*, 12:25–36 (1983).
Kit et al, *Biochem. Biophys. Res. Comm.*, 5:120–124 (1961).
Kit et al, *Herpesvirus*, 21:311–328 (1984).
Kit et al, *Exp. Cell Res.*, 31:297–321 (1963).
Kit et al, *Biochem. Biophys. Res. Comm.*, 13:500–504 (1963).
Kit et al, *Am. J. Vet. Res.*, 46:1359–1367 (1985).
Kit et al, *Biochemica et Biophysica Acta*, 741:158–170 (1983).
Kit et al, *Am. J. Vet. Res.*, 48:780–793 (1987).
Kit et al, *Biochem. Biophys. Res. Comm.*, 11:55–59 (1963).
Kit et al, *Progr. Med. Virol.*, 38:128–166 (1991).
Kit et al, *J. Mol. Biol.*, 6:22–33 (1963).
Kit et al, *Virol.*, 113:452–454 (1981).
Kit et al, *Virol.*, 130:381–389 (1983).
Kit et al, *Antimicrobial. Agents Chemother.*, 31:1483–1490 (1987).
Kit, *Proc. 90th Anin. Mtg. of the U.S. Anim. Hlth. Assoc.*, Lousiville, KY, pp. 105–126 (1986).
Kit, *13th International Cancer Congress*, Part C, Biology of Cancer (2), pp. 327–336, Alan R. Liss, Inc., N.Y. (1983).
Klien, *Arch. Virol.*, 72:143–168 (1982).
Klupp et al, *Virol.*, 182:732–741 (1991).
Kominari et al, *Nucl. Acid Res.*, 10:1963–1979 (1982) (Abstract).
Kiprowski et al, *Vir. Immun.*, Academic Press, Chapter 8, p. 122 (1975).
Kriss et al, *Biochem. Pharm.*, 13:365–370 (1964).
Kwoh et al, *J. Mol. Appl. Genet.*, 2:191–200 (1983).
Ladin et al, *Virol.*, 116:544–561 (1982).
Larson et al, *Nucleic Acids Res.*, 10(1):39–49, Contents and Subject Index (pp. 8374–8375) (1982).
Lai et al, *Virology*, 60:466–475 (1972).
Lewis et al, *Mol. Cell. Biol.*, 3(10):1815–1823 (1983).
Littler et al, *EMBO J.*, 5:1959–1966 (1986).
Lobmann et al, *Am. J. Vet. Res.*, 45:2498–2503 (1984).
Lomniczi et al, *Virol.*, 161:181–189 (1987).
Lomniczi et al, *J. of Virol.*, 49:970–979 (1984).
Lomniczi et al, *J. Virol.*, 52:198–205 (1984).
Lomonte et al, *Arch. Virol.*, 127:327–337 (1992).
Lui et al, *Gene*, 44:279–295 (1986).
Lycke et al, *Textbook of Medical Virology*, Butterworth & Co., p. 228 (1983).
Mackett et al, *PNAS*, 79:7415–7419 (1982).
Mackett et al, *J. of Virol.*, 49(3):857–864 (1984).
Maga et al, *Biochem. J.*, 294:381–385 (1993).
Maitland et al, *Cell*, 11:233–241 (1977).
Marchioli et al, *J. Virol.*, 61:3977–3982 (1987).
Marchioli et al, *Am. J. Vet. Res.*, 48(11):1577–1583 (1987).
Marsden et al, *J. Virol.*, 46:434–445 (1983).
Maxam et al, *In Methods in Enzymology*, 65(I):499 (1980).
Mayfield et al, *J. Virol.*, 47:259–264 (1983).
McGregor et al, *Am. J. Vet. Res.*, 46:1494–1497 (1985).
McKnight, *Nucl. Acids Res.*, 8:5949–5964 (1980).
McLauchlan et al, *Nucl. Acids Res.*, 10:501–512 (1982).
Maeda et al, *J. Biol. Chem.*, 257:2806–2815 (1982) (Abstract).
Meignier et al, *J. Infect. Dis.*, 162:313–321 (1990).
Mettenleiter, *Acta Veterinaria Hungarica*, 42(2–3):153–177 (1994).

Mettenleiter et al, *J. of Virol.*, 56:307–311 (1985).
Mettenleiter et al, *J. Virol.*, 62:12–19 (1988).
Miller et al, *Virology*, 18:824–832 (1976).
Miller et al, *Am. J. Vet. Res.*, 56:870–874 (1995).
Mizusawa et al, *Nucl. Acid Res.*, 14:1319–1324 (1986).
Mocarski et al, *Cell*, 22:243–255 (1980).
Molitor et al, *Swine*, 9:F409–F416 (1987).
Moormann et al, *J. Gen. Virol.*, 71:1591–1595 (1990).
Moss et al, *J. Virol.*, 23(2):234–239 (1977).
Murchie et al, *J. Gen. Virol.*, 62:1–15 (1982).
Nakano et al, *PNAS*, 79:1593–1596 (1982).
Narita et al, *Am. J. Vet. Res.*, 50:1940–1945 (1989).
Narita et al, *J. Comp. Path.*, 102:61–69 (1990).
Needleman et al, *J. Mol. Biol.*, 48:443–453 (1970).
Nunberg et al, *J. Virol.*, 63:3240–3249 (1989).
Otsuka et al, *Antiviral Res.*, 2:301–311 (1982).
Otsuka et al, *Virology*, 135:316–330 (1984).
Otsuka et al, *Virol.*, 113:196–213 (1981).
Panicalli et al, *PNAS*, 79:4927–4931 (1982).
Paul et al, *Archives of Virol.*, 73:193–198 (1982).
Peeters et al, *J. Virol.*, 66:3888–3892 (1992).
Post et al, *Cell*, 24:555–565 (1981).
Post et al, *Cell*, 25:227–232 (1981).
Prieto et al, *J. Gen. Virology*, 72:1435–1439 (1991).
Pringle et al, *Virol.*, 55:495 (1973).
Read et al, *Virol.*, 138:368–372 (1984).
Reyes et al, *J. Gen. Virology*, 62:191–206 (1982).
Rixon et al, *Virol.*, 97:151–163 (1979).
Robbins et al, *J. Mol. Appl. Genet.*, 2:485–496 (1984).
Roizman, *The Herpesviruses, The Family Herpesviridae: General Description, Taxonomy and Classification*, Plenum Press, New York (1982).
Roizman et al, *Science*, 229:1208–1214 (1985).
Rouh et al, *J. Virol.*, 65:621–631 (1991).
Sanders et al, *J. Gen. Virol.*, 63:277–295 (1982).
Sanger et al, *J. Mol. Biol.*, 94:441–448 (1975).
Sanger et al, *Proc. Natl. Acad. Sci.*, 74(12):5463–5467 (1977).
Sargentini et al, *Mutation Res.*, 154:1–27 (1985).
Sawyer et al, *J. Gen. Virol.*, 69:2585–2593 (1988).
Scott et al, *J. Gen. Virol.*, 70:3055–3065 (1989).
Sedarati et al, *J. Gen. Virol.*, 68:2389–2395 (1987).
Silverstein et al, *Proc. Natl. Acad. Sci. USA*, 70(7):2101–2104 (1973).
Speicher et al., *J. Biol. Chem.*, 258:14938–14947 (1983) (Abstract).
Skoda et al, *Acta Virol.*, 6:189 (1962).
Skoda et al, *Acta Virol.*, 8:123–134 (1964).
Skoda et al, *Acta Virol.*, 8:1–9 (1964).
Smiley, *Nature*, 285:333–335 (1980).
Smith et al, *Biotech. and Gen. Eng. Rev.*, 2:383–407 (1984).
Smith, *Mutation Res.*, 277:139–162 (1992).
Stegeman et al, *The Veterinary Record*, pp. 327–330 (1994).
Stevens et al, *Biochem. Biophys. Res. Com.*, 10:63–66 (1963).
Stewart et al, *Nucl. Acids Res.*, 11:629–646 (1983) (Abstract).
Stinski et al, *J. Virol.*, 46(1):1–14 (1983).
Stow et al, *J. Virology*, 28:182–192 (1978).
Stow et al, *J. Gen. Virol.*, 33:447–458 (1976).
Stringer et al, *J. Virol.*, 21(3):889–901 (1977).
Summers et al, *Proc. Natl. Acad. Sci. USA*, 72(10):4081–4084 (1975).
Swain et al, *J. Virology*, 46:1045–1050 (1983).

Takashi et al, *Proc. Natl. Acad. Sci., USA*, 79:2850–2854 (1982) (Abstract).
Tatarov, *Cah. Med. Vet.*, 43:347–352 (1974).
Tatarov, *Vet. Nauki*, 15(8):847–853 (1968).
Tatarov et al, *Vet. Sci.*, 18:3–12 (1981).
Tatarov et al, *Vet. Nauki*, 6:49–54 (1969).
Tatarov et al, *Vet. Sbirka*, 7:10–12 (1974).
Tenser et al, *Abstr. Annu. Meet. Am. Soc. Microbiol.*, Abstract S57, p. 244 (1982).
Tenser et al, *In Virology*, 112:328–341 (1981).
Tenser et al, *Virology*, 155:257–261 (1986).
Tenser et al, *Virology*, 112:328–341 (1981).
Tenser et al, *J. Clin. Micro.*, 17:122–127 (1983).
Tenser et al, *J. Infect. Dis.*, 151:548–550 (1985).
Tenser et al, *J. Gen. Virol.*, 64:1369–1373 (1983).
Thayer, *Boehringer–Mannheim Biochemicals*, Newsletter, p. 10 (1986).
Thomsen et al, *J. Virol.*, 61(1):229–232 (1987).
Tikoo et al, *Advances in Virus Research*, 45:191–223 (1994).
Toma et al, *Rec. Méd. Vét.*, 155(2):131–137 (1979).
Van Santen et al, *J. Virol.*, 46(2):424–433 (1983).
Van–Oirschot et al, *Vet. G.*, 6:225–229 (1984).
Wagner et al, *J. Virol.*, 4:36–46 (1969).
Wagner et al, *Biochem.*, 64:626–633 (1969).
Wagner et al, *Proc. Nat'l. Acad. Sciences USA*, 78:1441–1445 (1981).
Watson et al, *Nucleic Acids Res.*, 9(16):4189–4199 (1981).
Watson et al, *J. Virol.*, 37(1):431–444 (1981).
Weir et al, *PNAS*, 79:1210–1214 (1982).
Wigler et al, *Cell*, 11:223–232 (1977).
Wilbur et al, *PNAS, USA*, 80:726–730 (1983).
Zang et al, *BioTechniques*, 14(3):376–377 (1993).
Declaration of Dr. Saul Kit.
"Materials Transfer Agreement" of Pennsylvania State University College of Medicine, at Hershey.
"Materials Transfer Agreement" and Biological Materials Agreement for Research Use of Vanderbilt University, Nashville, Tenn.
"Declaration of Bela Lomniczi" executed May 23, 1996.
Applied Biosystems catalog, Table of Contents and pp. 136–138.
Lomniczi et al, In: *Vaccination and Control of Aujeszky's Disease*, Ed. Van Oirschot, Kluwer Academic Publishers, pp. 93–102 (1989).
Ben–Porat et al, *Herpesvirus*, Alan R. Liss, Inc., pp. 537–550 (1984).
Ben–Porat et al, In: *The Herpesviruses*, vol. 3, Ed. Bernard Roizman, Plenumn Press, pp. 105–173 (1982).
Todd et al, *Arch. Virol.*, 86:167–176 (1985).
Schoenbaum et al, *Am. J. Vet. Res.*, 51(3):334–338 (1990).
Bass, *Proc. US Animal Health Assoc.*, pp. 426–431 (1978).
Tatarov, *Tijdschrift voor Diergeneeskunde*, 108:204–209 (1983).
Bakersville et al, *The Veterinary Bulletin*, 43:464–480 (1973).
Kit et al, *Acta Veterinaria Hungarica*, 42:(2–3):319–330 (1994).
Thompson et al, *Virology*, 131:180–192 (1983).
Van Alstine et al, *JAVMA*, 185(4):409–410 (1984).
Klein et al, *Archives of Virology*, 65:237–246 (1980).
Cappel et al, *Archives of Virology*, 73:61–67 (1982).
McDougall et al, *Journal of Virology*, 33(9):1221–1224 (1980).

B1 4,514,497

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 21–24, 26–29, and 31–39 is confirmed.

Claims 1–20 were previously disclaimed.

Claims 25 and 30 are determined to be patentable as amended.

25. The temperature-resistant pseudorabies virus which fails to produce any functional TK as in [claim 103] *claim 21*, wherein said virus is [lympholized] *lyophilized*.

30. The temperture-resistant pseudorabies virus which fails to produce any functional TK as in claim 26, wherein said virus is [lypholized] *lyophil